(12) United States Patent
Hemming et al.

(10) Patent No.: US 12,161,475 B2
(45) Date of Patent: *Dec. 10, 2024

(54) STATE-BASED ATRIAL EVENT DETECTION

(71) Applicant: Medtronic, Inc., Minneapolis, MN (US)

(72) Inventors: Michael T. Hemming, Kiowa, CO (US); Saul E. Greenhut, Aurora, CO (US)

(73) Assignee: Medtronic, Inc., Minneapolis, MN (US)

( * ) Notice: Subject to any disclaimer, the term of this patent is extended or adjusted under 35 U.S.C. 154(b) by 1205 days.

This patent is subject to a terminal disclaimer.

(21) Appl. No.: 16/910,832

(22) Filed: Jun. 24, 2020

(65) Prior Publication Data

US 2020/0315481 A1 Oct. 8, 2020

Related U.S. Application Data

(63) Continuation of application No. 15/786,832, filed on Oct. 18, 2017, now Pat. No. 10,694,967.

(51) Int. Cl.
*A61B 5/0205* (2006.01)
*A61B 5/00* (2006.01)
(Continued)

(52) U.S. Cl.
CPC ............ *A61B 5/361* (2021.01); *A61B 5/0031* (2013.01); *A61B 5/316* (2021.01); *A61B 5/318* (2021.01);
(Continued)

(58) Field of Classification Search
CPC ......... A61B 5/361; A61B 5/318; A61B 5/363; A61B 5/352; A61B 5/316; A61B 5/0031;
(Continued)

(56) References Cited

U.S. PATENT DOCUMENTS

| 4,374,382 A | 2/1983 | Markowitz |
| 4,428,378 A | 1/1984 | Anderson et al. |

(Continued)

FOREIGN PATENT DOCUMENTS

| EP | 0597728 A2 | 5/1994 |
| EP | 0726082 A2 | 8/1996 |

(Continued)

OTHER PUBLICATIONS

Chirife M.D., et al., "Prediction of Interatrial and Interventricular Electromechanical delays from P/QRS Measurements: Value for Pacemaker Timing Optimization", Feb. 2008, Pacing and Clinical Electrophysiology: Pace, vol. 31, No. 2, pp. 177-183.

(Continued)

*Primary Examiner* — Lindsey G Wehrheim
(74) *Attorney, Agent, or Firm* — Shumaker & Sieffert, P.A.

(57) ABSTRACT

An implantable medical device includes a memory storing criteria for transitioning between states of a cardiac cycle model, the states including a P-wave state. The device also includes sensing circuitry that senses a cardiac signal that varies as a function of a cardiac cycle of a patient, and also includes processing circuitry coupled to the sensing circuitry. The processing circuitry is configured to detect an R-wave in the sensed cardiac signal, to determine an elapsed time since the detection of the R-wave, to determine one or more morphological values of a post-R-wave segment of the cardiac signal to compare the elapsed time and the one or more morphological values to the stored criteria for transitioning between the plurality of states of the cardiac cycle model, and to detect a P-wave in the sensed cardiac signal in response to a transition to the P-wave state of the cardiac cycle model.

23 Claims, 10 Drawing Sheets

(51) Int. Cl.

| | | |
|---|---|---|
| *A61B 5/024* | (2006.01) | |
| *A61B 5/316* | (2021.01) | |
| *A61B 5/318* | (2021.01) | |
| *A61B 5/352* | (2021.01) | |
| *A61B 5/361* | (2021.01) | |
| *A61B 5/363* | (2021.01) | |
| *A61N 1/365* | (2006.01) | |
| *A61N 1/372* | (2006.01) | |
| *A61N 1/375* | (2006.01) | |
| *A61N 1/39* | (2006.01) | |
| *A61B 5/02* | (2006.01) | |
| *A61N 1/362* | (2006.01) | |

(52) U.S. Cl.
CPC ............. *A61B 5/352* (2021.01); *A61B 5/363* (2021.01); *A61B 5/686* (2013.01); *A61B 5/726* (2013.01); *A61N 1/36507* (2013.01); *A61N 1/36521* (2013.01); *A61N 1/37211* (2013.01); *A61N 1/3756* (2013.01); *A61N 1/39622* (2017.08); *A61B 5/02028* (2013.01); *A61B 5/0205* (2013.01); *A61B 5/02405* (2013.01); *A61N 1/3622* (2013.01)

(58) Field of Classification Search
CPC ..... A61B 5/686; A61B 5/726; A61B 5/02028; A61B 5/0205; A61B 5/02405; A61N 1/39622; A61N 1/36507; A61N 1/36521; A61N 1/37211; A61N 1/3756; A61N 1/3622
See application file for complete search history.

(56) References Cited

U.S. PATENT DOCUMENTS

| | | |
|---|---|---|
| 4,481,950 A | 11/1984 | Duggan |
| 4,543,955 A | 10/1985 | Schroeppel |
| 4,787,389 A | 11/1988 | Tarjan |
| 5,052,388 A | 10/1991 | Sivula et al. |
| 5,113,859 A | 5/1992 | Funke |
| 5,117,824 A | 6/1992 | Keimel et al. |
| 5,179,949 A | 1/1993 | Rife |
| 5,251,626 A | 10/1993 | Nickolls et al. |
| 5,280,792 A | 1/1994 | Leong et al. |
| 5,312,445 A | 5/1994 | Nappholz et al. |
| 5,354,316 A | 10/1994 | Keimel |
| 5,374,280 A | 12/1994 | Den Dulk |
| 5,402,070 A | 3/1995 | Shelton et al. |
| 5,411,535 A | 5/1995 | Fujii et al. |
| 5,507,782 A | 5/1996 | Kieval |
| 5,545,186 A | 8/1996 | Olson et al. |
| 5,620,474 A | 4/1997 | Koopman |
| 5,626,140 A | 5/1997 | Feldman et al. |
| 5,660,183 A | 8/1997 | Chiang et al. |
| 5,683,432 A | 11/1997 | Goedeke |
| 5,690,689 A | 11/1997 | Sholder |
| 5,690,691 A | 11/1997 | Chen et al. |
| 5,741,308 A | 4/1998 | Sholder |
| 5,755,739 A | 5/1998 | Sun et al. |
| 5,794,624 A | 8/1998 | Kwong |
| 5,814,089 A | 9/1998 | Stokes et al. |
| 5,855,593 A | 1/1999 | Olson et al. |
| 5,893,882 A | 4/1999 | Peterson et al. |
| 5,902,326 A | 5/1999 | Lessar et al. |
| 5,954,649 A | 9/1999 | Chia et al. |
| 6,016,448 A | 1/2000 | Busacker et al. |
| 6,108,579 A | 8/2000 | Snell et al. |
| 6,167,307 A | 12/2000 | Hess |
| 6,192,273 B1 | 2/2001 | Gel et al. |
| 6,206,847 B1 | 3/2001 | Edwards et al. |
| 6,208,894 B1 | 3/2001 | Schulman et al. |
| 6,263,242 B1 | 7/2001 | Mika et al. |
| 6,292,693 B1 | 9/2001 | Darvish et al. |
| 6,298,261 B1 | 10/2001 | Rex |
| 6,324,427 B1 | 11/2001 | Florio |
| 6,393,316 B1 | 5/2002 | Gillberg et al. |
| 6,477,415 B1 | 11/2002 | Yerich |
| 6,477,420 B1 | 11/2002 | Struble et al. |
| 6,508,771 B1 | 1/2003 | Padmanabhan et al. |
| 6,522,915 B1 | 2/2003 | Ceballos et al. |
| 6,592,519 B1 | 7/2003 | Martinez |
| 6,622,046 B2 | 9/2003 | Fraley et al. |
| 6,628,989 B1 | 9/2003 | Penner et al. |
| 6,687,685 B1 | 2/2004 | Sadeghi et al. |
| 6,738,668 B1 | 5/2004 | Mouchawar et al. |
| 6,754,528 B2 | 6/2004 | Bardy et al. |
| 6,764,446 B2 | 7/2004 | Wolinsky et al. |
| 6,772,005 B2 | 8/2004 | Casavant |
| 6,876,881 B2 | 4/2005 | Baumann et al. |
| 6,904,315 B2 | 6/2005 | Pan ken et al. |
| 6,931,279 B2 | 8/2005 | Ousdigian et al. |
| 6,948,950 B2 | 9/2005 | Yamaguchi |
| 7,024,248 B2 | 4/2006 | Penner et al. |
| 7,031,772 B2 | 4/2006 | Condie |
| 7,079,895 B2 | 7/2006 | Verbeek et al. |
| 7,149,577 B2 | 12/2006 | Sharma |
| 7,181,284 B2 | 2/2007 | Burnes et al. |
| 7,198,603 B2 | 4/2007 | Penner et al. |
| 7,209,790 B2 | 4/2007 | Thompson et al. |
| 7,218,965 B2 | 5/2007 | Casavant |
| 7,248,924 B2 | 7/2007 | Casavant |
| 7,254,442 B2 | 8/2007 | Van Gelder et al. |
| 7,283,874 B2 | 10/2007 | Penner |
| 7,505,813 B1 | 3/2009 | Gill et al. |
| 7,515,960 B2 | 4/2009 | Sharma |
| 7,532,929 B2 | 5/2009 | Mussig et al. |
| 7,558,631 B2 | 7/2009 | Cowan et al. |
| 7,606,621 B2 | 10/2009 | Brisken et al. |
| 7,610,092 B2 | 10/2009 | Cowan et al. |
| 7,623,911 B2 | 11/2009 | Sarkar |
| 7,634,313 B1 | 12/2009 | Kroll et al. |
| 7,689,279 B2 | 3/2010 | Ziegler |
| 7,702,390 B1 | 4/2010 | Min |
| 7,706,879 B2 | 4/2010 | Burnes et al. |
| 7,711,421 B2 | 5/2010 | Shafer et al. |
| 7,742,812 B2 | 6/2010 | Ghanem et al. |
| 7,774,063 B2 | 8/2010 | Ghanem et al. |
| 7,869,876 B2 | 1/2011 | Prakash |
| 7,881,791 B2 | 2/2011 | Sambelashvili et al. |
| 7,894,886 B2 | 2/2011 | Ghanem et al. |
| 7,904,153 B2 | 3/2011 | Greenhut et al. |
| 7,925,343 B1 | 4/2011 | Min et al. |
| 7,930,027 B2 | 4/2011 | Prakash et al. |
| 7,930,031 B2 | 4/2011 | Penner |
| 7,941,218 B2 | 5/2011 | Sambelashvili et al. |
| 7,945,064 B2 | 5/2011 | O'Brien, Jr. et al. |
| 7,991,467 B2 | 8/2011 | Markowitz et al. |
| 8,145,308 B2 | 3/2012 | Sambelashvili et al. |
| 8,160,684 B2 | 4/2012 | Ghanem et al. |
| 8,170,666 B2 | 5/2012 | Sheldon |
| 8,204,590 B2 | 6/2012 | Sambelashvili et al. |
| 8,214,041 B2 | 7/2012 | Van Gelder et al. |
| 8,233,980 B2 | 7/2012 | Pei |
| 8,275,432 B2 | 9/2012 | Kuhn et al. |
| 8,352,025 B2 | 1/2013 | Jacobson |
| 8,364,276 B2 | 1/2013 | Willis |
| 8,391,964 B2 | 3/2013 | Musley et al. |
| 8,401,629 B2 | 3/2013 | Stadler |
| 8,428,716 B2 | 4/2013 | Mullen et al. |
| 8,433,409 B2 | 4/2013 | Johnson et al. |
| 8,452,402 B2 | 5/2013 | Ecker et al. |
| 8,457,742 B2 | 7/2013 | Jacobson |
| 8,521,268 B2 | 8/2013 | Zhang et al. |
| 8,532,785 B1 | 9/2013 | Crutchfield et al. |
| 8,540,631 B2 | 9/2013 | Penner et al. |
| 8,541,131 B2 | 9/2013 | Lund et al. |
| 8,617,082 B2 | 12/2013 | Zhang et al. |
| 8,639,333 B2 | 1/2014 | Stadler et al. |
| 8,652,048 B2 | 2/2014 | Skerl et al. |
| 8,666,505 B2 | 3/2014 | O'Brien et al. |
| 8,676,289 B2 | 3/2014 | Ghanem et al. |
| 8,744,572 B1 | 6/2014 | Greenhut et al. |

(56) References Cited

U.S. PATENT DOCUMENTS

| | | |
|---|---|---|
| 8,768,459 B2 | 7/2014 | Ghosh et al. |
| 8,798,745 B2 | 8/2014 | Jacobson |
| 8,886,307 B2 | 11/2014 | Sambelashvili et al. |
| 8,923,963 B2 | 12/2014 | Bonner et al. |
| 9,008,776 B2 | 4/2015 | Cowan et al. |
| 9,566,012 B2 | 2/2017 | Greenhut et al. |
| 9,566,013 B2 | 2/2017 | Sambelashvili |
| 9,717,923 B2 | 8/2017 | Thomson-Nauman et al. |
| 10,694,967 B2 * | 6/2020 | Hemming .......... A61N 1/36507 |
| 2004/0147966 A1 | 7/2004 | Ding et al. |
| 2004/0186523 A1 | 9/2004 | Florio |
| 2004/0193223 A1 | 9/2004 | Kramer et al. |
| 2004/0215254 A1 | 10/2004 | Boule et al. |
| 2004/0215262 A1 | 10/2004 | Ferek-Petric |
| 2004/0230243 A1 | 11/2004 | Haefner et al. |
| 2005/0027321 A1 | 2/2005 | Ferek-Petric |
| 2005/0131480 A1 | 6/2005 | Kramer et al. |
| 2005/0209648 A1 | 9/2005 | Burnes et al. |
| 2006/0047319 A1 | 3/2006 | Bruhns et al. |
| 2006/0116592 A1 | 6/2006 | Zhou et al. |
| 2006/0116595 A1 | 6/2006 | Palreddy et al. |
| 2006/0116596 A1 | 6/2006 | Zhou et al. |
| 2006/0235478 A1 | 10/2006 | Van Gelder et al. |
| 2007/0129762 A1 | 6/2007 | Worley |
| 2007/0208386 A1 | 9/2007 | Kramer et al. |
| 2007/0239043 A1 | 10/2007 | Patel et al. |
| 2008/0009909 A1 | 1/2008 | Sathaye et al. |
| 2008/0082133 A1 | 4/2008 | Zhou |
| 2008/0228234 A1 | 9/2008 | Stancer |
| 2008/0269816 A1 | 10/2008 | Prakash et al. |
| 2008/0269823 A1 | 10/2008 | Burnes et al. |
| 2008/0294210 A1 | 11/2008 | Rosero |
| 2009/0234411 A1 | 9/2009 | Sambelashvili et al. |
| 2009/0234412 A1 | 9/2009 | Sambelashvili |
| 2009/0234413 A1 | 9/2009 | Sambelashvili et al. |
| 2009/0234414 A1 | 9/2009 | Sambelashvili et al. |
| 2009/0234415 A1 | 9/2009 | Sambelashvili et al. |
| 2009/0248103 A1 | 10/2009 | Sambelashvili et al. |
| 2009/0281587 A1 | 11/2009 | Pei |
| 2010/0016914 A1 | 1/2010 | Mullen et al. |
| 2010/0023078 A1 | 1/2010 | Dong et al. |
| 2010/0185111 A1 | 7/2010 | Miller |
| 2010/0198291 A1 | 8/2010 | Sambelashvili et al. |
| 2010/0228308 A1 | 9/2010 | Cowan et al. |
| 2010/0286541 A1 | 11/2010 | Musley et al. |
| 2011/0071586 A1 | 3/2011 | Jacobson |
| 2011/0125078 A1 | 5/2011 | Denison et al. |
| 2011/0190841 A1 | 8/2011 | Sambelashvili et al. |
| 2011/0196444 A1 | 8/2011 | Prakash et al. |
| 2012/0035685 A1 | 2/2012 | Saha et al. |
| 2012/0109235 A1 | 5/2012 | Sheldon et al. |
| 2012/0109236 A1 | 5/2012 | Jacobson et al. |
| 2012/0109675 A1 | 5/2012 | Ziegler et al. |
| 2012/0172892 A1 | 7/2012 | Grubac et al. |
| 2012/0263218 A1 | 10/2012 | Dal Molin et al. |
| 2012/0296228 A1 | 11/2012 | Zhang et al. |
| 2012/0316613 A1 | 12/2012 | Keefe et al. |
| 2013/0006622 A1 | 1/2013 | Khalil et al. |
| 2013/0013017 A1 | 1/2013 | Mullen et al. |
| 2013/0035748 A1 | 2/2013 | Bonner |
| 2013/0066169 A1 | 3/2013 | Rys et al. |
| 2013/0103109 A1 | 4/2013 | Jacobson |
| 2013/0116738 A1 | 5/2013 | Samade et al. |
| 2013/0131750 A1 | 5/2013 | Stadler et al. |
| 2013/0131751 A1 | 5/2013 | Stadler et al. |
| 2013/0138006 A1 | 5/2013 | Bomzin et al. |
| 2013/0197599 A1 | 8/2013 | Sambelashvili et al. |
| 2013/0218223 A1 | 8/2013 | Ghosh et al. |
| 2013/0218224 A1 | 8/2013 | Ghosh et al. |
| 2013/0218225 A1 | 8/2013 | Ghosh et al. |
| 2013/0218226 A1 | 8/2013 | Ghosh et al. |
| 2013/0218227 A1 | 8/2013 | Ghosh et al. |
| 2013/0226259 A1 | 8/2013 | Penner |
| 2013/0231710 A1 | 9/2013 | Jacobson |
| 2013/0268017 A1 | 10/2013 | Zhang et al. |
| 2014/0005740 A1 | 1/2014 | Ghosh et al. |
| 2014/0107723 A1 | 4/2014 | Hou et al. |
| 2014/0114372 A1 | 4/2014 | Ghosh et al. |
| 2014/0121720 A1 | 5/2014 | Bonner et al. |
| 2014/0163635 A1 | 6/2014 | Ghosh et al. |
| 2014/0236253 A1 | 8/2014 | Ghosh et al. |
| 2014/0276928 A1 | 9/2014 | Vanderpool et al. |
| 2014/0277233 A1 | 9/2014 | Ghosh |
| 2014/0277245 A1 | 9/2014 | Lu et al. |
| 2014/0277246 A1 | 9/2014 | Lu et al. |
| 2014/0330208 A1 | 11/2014 | Christie et al. |
| 2014/0330287 A1 | 11/2014 | Thompson-Nauman et al. |
| 2014/0330326 A1 | 11/2014 | Thompsen-Naumann et al. |
| 2014/0358135 A1 | 12/2014 | Sambelashvili et al. |
| 2015/0142069 A1 | 5/2015 | Sambelashvili |
| 2015/0142070 A1 | 5/2015 | Sambelashvili |
| 2016/0310031 A1 | 10/2016 | Sarkar |
| 2017/0014629 A1 | 1/2017 | Ghosh et al. |
| 2019/0110707 A1 | 4/2019 | Hemming et al. |

FOREIGN PATENT DOCUMENTS

| | | |
|---|---|---|
| EP | 1629863 A1 | 3/2006 |
| WO | 2001058518 A3 | 1/2002 |
| WO | 0247761 A2 | 6/2002 |
| WO | 2012128836 A1 | 9/2012 |

OTHER PUBLICATIONS

Hawkins, "Epicardial Wireless Pacemaker for Improved Left Ventricular Reynchronization (Conceptual Design)", Dec. 2010, A Thesis presented to the Faculty of California Polytechnic State University, San Luis Obispo, 57 pp.

"St. Jude's Quadra Assura MP with MultiPoint Pacing Gets European Go Ahead," Cardiac Surgery, Jun. 24, 2013, http://www.medgadget.com/2013/06/st-judes-quadra-assura-mp-with-multipoint-pacing-gets-european-go-ahead.html, 2 pp.

Prosecution History from U.S. Appl. No. 15/786,832, dated Sep. 24, 2019 through Feb. 24, 2020, 37 pp.

* cited by examiner

STATE-BASED ATRIAL EVENT DETECTION

STATE-BASED ATRIAL EVENT DETECTION

This application is a continuation of U.S. patent application Ser. No. 15/786,832 (issued as U.S. Pat. No. 10,694,967), filed on Oct. 18, 2017, the entire content of which is incorporated herein by reference.

TECHNICAL FIELD

This disclosure relates to medical devices and, more particularly, to medical devices that monitor physiological conditions of a patient.

BACKGROUND

Implantable pacemakers and cardioverter defibrillators (ICDs) are available for delivering electrical stimulation therapies to a patient's heart, such as bradycardia pacing, cardiac resynchronization therapy (CRT), anti-tachycardia pacing and cardioversion/defibrillation shocks. Medical device technology advancement has led toward smaller and smaller implantable devices. Recently, cardiac pacemakers have been introduced which can be implanted directly in a heart chamber. In some examples, such pacemakers may be leadless and delivered into the heart chamber using a catheter. Such miniaturized pacemakers may be referred to as intracardiac pacing devices (PDs), although they may be epicardially or extracardially implanted, in some examples. The introduction of such PDs, and the resulting elimination of the need for transvenous intracardiac leads, provides several advantages. For example, complications due to infection associated with a lead extending from a subcutaneous pacemaker pocket transvenously into the heart can be eliminated. Other complications, such as "twiddler's syndrome," lead fracture, or poor connection of the lead to the pacemaker are eliminated in the use of an intracardiac PD.

Various technologies are directed to controlling an intracardiac PD to deliver pacing pulses in synchrony with paced or sensed events occurring in other heart chambers. Cardiac resynchronization therapy (CRT) is an example of a pacing therapy that includes delivering pacing pulses in a heart chamber at a predetermined time interval after a sensed or paced event in another heart chamber. CRT is a treatment for heart failure patients in whom one or more heart chambers are electrically paced to restore or improve heart chamber synchrony. Improved heart chamber synchrony is expected to alleviate symptoms of heart failure.

Achieving a positive clinical benefit from CRT, however, may be dependent on several therapy control parameters, such as the timing intervals used to control pacing pulse delivery to one or both ventricles, e.g., an atrio-ventricular (AV) interval and/or an inter-ventricular (VV) interval. The AV interval controls the timing of ventricular pacing pulses relative to a preceding atrial depolarization, intrinsic or paced. The VV interval controls the timing of a pacing pulse in one ventricle relative to a paced or intrinsic sensed event in the other ventricle. Pacing may be delivered in the right ventricle (RV) and/or the left ventricle (LV) to restore ventricular synchrony.

CRT includes delivering pacing stimuli to both ventricles, or to one ventricle with the intended result of a substantially simultaneous mechanical contraction and ejection of blood from the ventricles. Ideally, each pacing pulse stimulus delivered to a ventricle would evoke a response from the stimulated ventricle. In order to evoke the desired response, it is preferable to time the delivery of the ventricular pacing so as to be delivered at a target point in time subsequent to a P-wave of a cardiac cycle of the patient. If the ventricular pacing signal is delivered too late after a P-wave, then the pacing therapy may potentially coincide with the occurrence of an R-wave of the cardiac cycle of the patient.

SUMMARY

Many CRT techniques, and ventricular pacing techniques in general, include determining the time at which to deliver a ventricular pacing signal based on adding a delay after the last-sensed P-wave. As a result, P-wave sensing is an important factor in determining timing of the ventricular pacing. Furthermore, when an IMD system utilizes subcutaneous sensing or substernal sensing (thereby relying on far-field signals), the P-waves are often of low amplitude and frequency content. Thus, in many cases of subcutaneous or substernal sensing, detecting P-waves may be relatively difficult.

To address the potential problems discussed above, this disclosure provides systems configured to use state-based sequencing of a patient's cardiac cycle to detect P-waves, e.g., for timing of delivery of ventricular pacing, such as during CRT therapy. In various examples, the systems of this disclosure apply state-transition probabilities and use heuristics-driven training to detect a P-wave of the patient's cardiac cycle. As such, this disclosure describes enhanced P-wave detection systems that can, for example, be used to more effectively deliver ventricular pacing therapy coincident with, substantially coincident with, or prior to a subsequent R-wave.

In one example, the disclosure provides an implantable medical device that includes a memory, sensing circuitry, and processing circuitry coupled to the sensing circuitry. The memory is configured to store criteria for transitioning between a plurality of states of a cardiac cycle model, the plurality of states including a P-wave state. The sensing circuitry is configured to sense a cardiac signal that varies as a function of a cardiac cycle of a patient. The processing circuitry is configured to detect an R-wave in the sensed cardiac signal, to determine an elapsed time since the detection of the R-wave, and to determine one or more morphological values of a post-R-wave segment of the cardiac signal occurring after the detection of the R-wave. The processing circuitry is further configured to compare the elapsed time and the one or more morphological values to the stored criteria for transitioning between the plurality of states of the cardiac cycle model, and to detect a P-wave in the sensed cardiac signal in response to a transition to the P-wave state of the cardiac cycle model.

In another example, the disclosure provides a method that includes storing, to a memory of an implantable medical device (IMD), criteria for transitioning between a plurality of states of a cardiac cycle model, the plurality of states including a P-wave state and sensing, by sensing circuitry of the IMD, a cardiac signal that varies as a function of a cardiac cycle of a patient. The method further includes detecting, by processing circuitry of the IMD, an R-wave in the sensed cardiac signal, determining, by the processing circuitry of the IMD, an elapsed time since the detection of the R-wave, and determining, by the processing circuitry of the IMD, one or more morphological values of a post-R-wave segment of the cardiac signal occurring after the detection of the R-wave. The method further includes comparing, by the processing circuitry of the IMD, the elapsed time and the one or more morphological values to the stored criteria for transitioning between the plurality of states of the cardiac cycle model, and detecting, by the processing circuitry of the IMD, a P-wave in the sensed cardiac signal in response to a transition to the P-wave state of the cardiac cycle model.

In another example, the disclosure provides an implantable medical device that includes means for storing criteria for transitioning between a plurality of states of a cardiac cycle model, the plurality of states including a P-wave state and means for sensing a cardiac signal that varies as a function of a cardiac cycle of a patient. The implantable medical device further includes means for detecting an R-wave in the sensed cardiac signal, means for determining an elapsed time since the detection of the R-wave, means for determining one or more morphological values of a post-R-wave segment of the cardiac signal occurring after the detection of the R-wave, means for comparing the elapsed time and the one or more morphological values to the stored criteria for transitioning between the plurality of states of the cardiac cycle model, and means for detecting a P-wave in the sensed cardiac signal in response to a transition to the P-wave state of the cardiac cycle model.

In another example, this disclosure provides a non-transitory computer-readable storage medium encoded with instructions that, when executed, cause one or more processors of an implantable medical device to store, to the computer-readable storage medium, criteria for transitioning between a plurality of states of a cardiac cycle model, the plurality of states including a P-wave state, to sense, using sensing circuitry of the implantable medical device, a cardiac signal that varies as a function of a cardiac cycle of a patient, to detect an R-wave in the sensed cardiac signal, to determine an elapsed time since the R-wave, to determine one or more morphological values of a post-R-wave segment of the cardiac signal, to compare the elapsed time and the one or more morphological values to the stored criteria for transitioning between the plurality of states of the cardiac cycle model, and to detect a P-wave in the sensed cardiac signal in response to a transition to the P-wave state of the cardiac cycle model.

The systems of this disclosure provide one or more potential improvements over existing P-wave detection technology. By implementing state-based sequencing and exploiting state-transition probabilities, the systems of this disclosure use contextual information and likelihood determinations to detect a P-wave in time to potentially trigger a pacing signal that precedes or coincides with a subsequent intrinsic R-wave. As such, the systems of this disclosure may leverage P-wave detection using subcutaneous or substernal cardiac cycle-monitoring infrastructure to drive another device, such as an intracardiac PD, that delivers ventricular pacing, e.g., for CRT.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

DETAILED DESCRIPTION

This disclosure describes systems configured to use state-based sequencing of a patient's cardiac cycle to detect P-waves. The detected P-waves may be used for timing of delivery of ventricular pacing, e.g., during CRT therapy. Alternatively, the P-waves may be used for identifying atrial tachyarrthmias, e.g., atrial fibrillation (AF). In various examples, the systems of this disclosure use events that occur in a normal cardiac cycle to perform one or more modeling techniques (such as, but not limited to, Hidden Markov Process-based modeling) for expected variations of a patient's cardiac cycle, which may be sensed at some later time. The systems may define probability criteria for state transitions in the patient's cardiac cycle via a priori estimates. In some implementations, the systems of this disclosure may tune the state transition probability criteria via machine learning that uses probability information (e.g., Bayesian probabilities). To determine state transitions, the systems of this disclosure may use a combination of different inputs, such as an elapsed time since the last R-wave detected in the cardiac cycle, in addition to information characterizing the morphology of the cardiac electrogram, e.g., one or more wavelet-derived coefficients or coefficients derived from another filter transformation. The coefficients may be used as target filters to evaluate morphological values of the sensed cardiac signal, while the elapsed time since the last-detected R-wave may provide time-dependent context to the target filters.

Figure 1A:
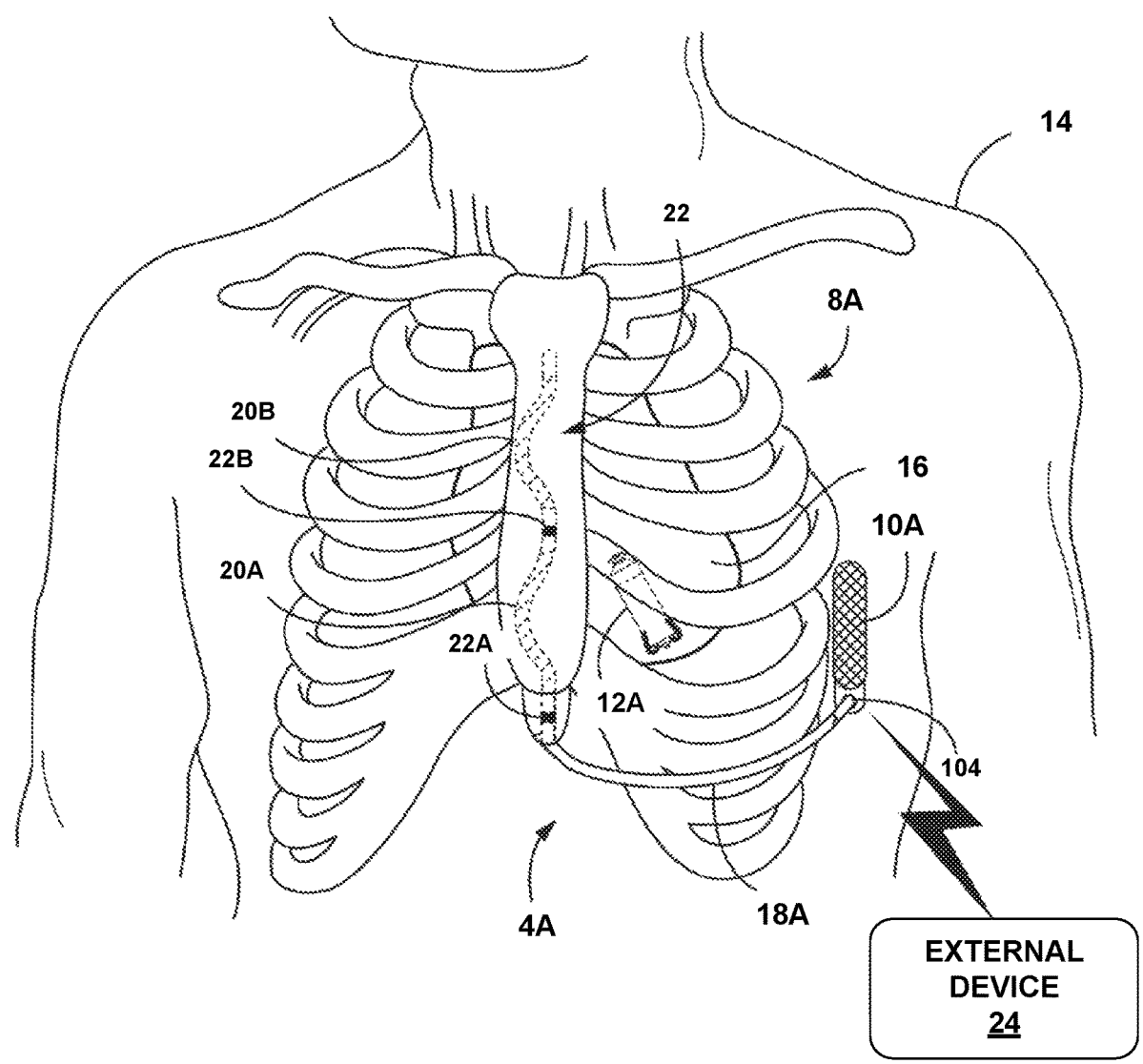
FIG. 1A is a conceptual diagram illustrating is an example front view of a patient implanted with an example medical device system that includes an extracardiovascular ICD system and a pacing device (PD) that is implanted within a cardiac chamber of the patient in accordance with one or more aspects of this disclosure.
Figure 1B:
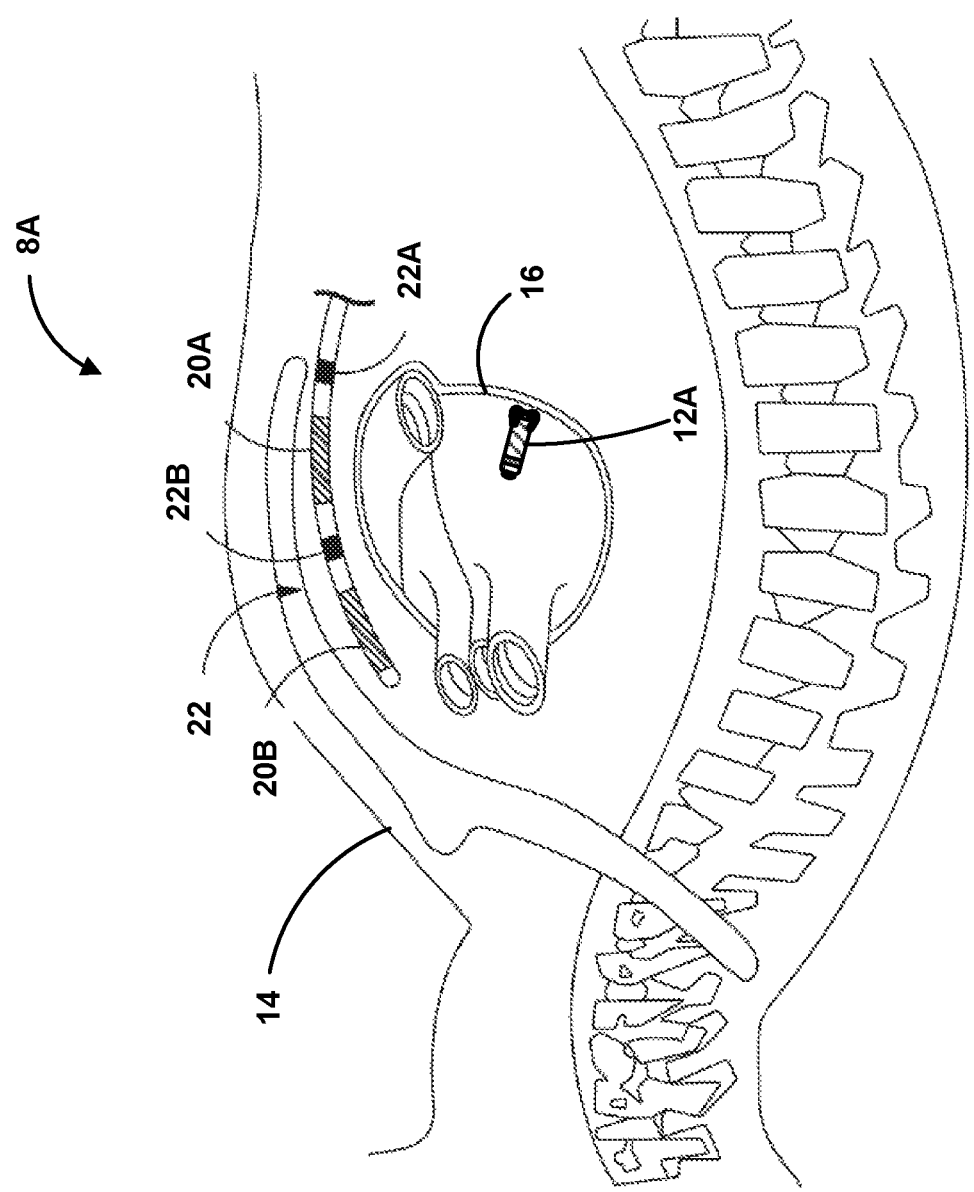
FIG. 1B is a conceptual diagram illustrating an example side view of a patient implanted with the example medical device system of FIG. 1A, in accordance with one or more aspects of this disclosure.
Figure 1C:
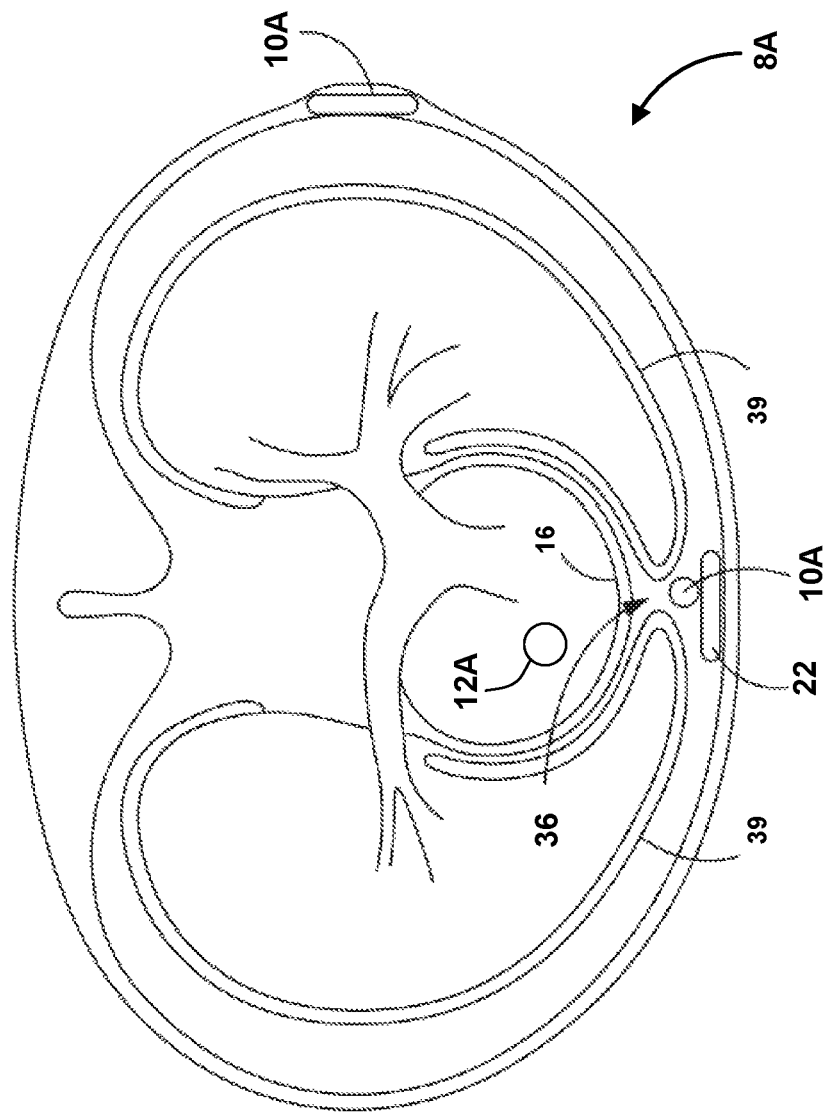
FIG. 1C is a conceptual diagram illustrating an example transverse view of a patient implanted with the example medical device system of FIG. 1A, in accordance with one or more aspects of this disclosure.

FIGS. 1A-1C are conceptual diagrams illustrating various views of an example cardiac medical device system 8A implanted within a patient 14. Components with like numbers in FIGS. 1A-1C may be similarly configured and may provide similar functionality. Medical device system 8A as illustrated in FIGS. 1A-1C may be configured to perform one or more of the techniques described herein with respect to P-wave detection.

FIG. 1A is a conceptual diagram illustrating is an example front view of a patient implanted with an example cardiac medical device system 8A that includes an extracardiovascular implantable cardioverter defibrillator (ICD) system 4A, and a pacing device (PD) 12A that is implanted within a cardiac chamber of patient 14 in accordance with one or more aspects of this disclosure. With respect to FIGS. 1A-1C, and elsewhere herein, PD 12A is generally described as being attached within a chamber of heart 16A. That is, PD 12A is described in various portions of this disclosure as represents an intracardiac pacing device. However, it will be appreciated that, in other examples that are consistent with aspects of this disclosure, PD 12A may be attached to an external surface of heart 16A, such that PD 16 is disposed outside of heart 16A, but is capable of pacing a desired chamber. In one example in which PD 12A is attached to an external surface of heart 16A, one or more components of PD 12A may be in contact with the epicardium of heart 16A. Therefore, although PD 12A is generally described herein as a pacing device for intracardiac implantation, PD 12A may alternatively be configured to attach to an external surface of heart 16A and operate as an extracardiac pacing device.

ICD system 4A includes ICD 10A that is connected to at least one implantable cardiac defibrillation lead 18A (hereinafter, "defibrillation lead 18A"). ICD 10A is configured to deliver high-energy cardioversion shocks or defibrillation pulses to heart 16A of patient 14, in response to atrial fibrillation or ventricular fibrillation being detected. Cardioversion shocks are typically delivered in synchrony with a detected R-wave, when fibrillation detection criteria are met. Defibrillation pulses are typically delivered when fibrillation criteria are met, and the R-wave cannot be discerned from signals sensed by ICD 10A.

ICD 10A of FIG. 1A may be implanted subcutaneously or submuscularly on the left side of patient 14 above the ribcage. Defibrillation lead 18A of FIG. 1A may be implanted at least partially in a substernal location in FIG. 1A, e.g., between the ribcage and/or sternum 22 and heart. In one such configuration, a proximal portion of defibrillation lead 18A extends subcutaneously from ICD 10A toward the sternum, and a distal portion of lead 18A extends under or below the sternum 22 in the anterior mediastinum 36 (see FIG. 1C). The anterior mediastinum 36 is bounded laterally by the pleurae 39 (see FIG. 1C), posteriorly by the pericardium, and anteriorly by the sternum 22. In some instances, the anterior wall of the anterior mediastinum 36 may also be formed by the transversus thoracis and one or more costal cartilages. The anterior mediastinum 36 includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of defibrillation lead 18A extends along the posterior side of the sternum 22 substantially within the loose connective tissue and/or substernal musculature of anterior mediastinum 36. Defibrillation lead 18A may be at least partially implanted in other intrathoracic locations, e.g., other non-vascular, extra-pericardial locations, including the gap, tissue, or other anatomical features around the perimeter of and adjacent to, but not attached to, the pericardium or other portion of heart 16A and not above the sternum 22 or ribcage.

In other examples, defibrillation lead 18A may be implanted at other extracardiovascular locations. For example, defibrillation lead 18A may extend subcutaneously above the ribcage from ICD 10A toward a center of the torso of patient 14, bend or turn near the center of the torso, and extend subcutaneously superior above the ribcage and/or sternum 22, similar to that shown in FIG. 1A. Defibrillation lead 18A may be offset laterally to the left or the right of the sternum 22 or located over the sternum 22. Defibrillation lead 18A may extend substantially parallel to the sternum 22 or be angled lateral from the sternum 22 at either the proximal or distal end. In another example, defibrillation lead 18A and/or a pacing lead or sensing lead may be implanted within the pericardial sac of heart 16A, within the pericardium of heart 16A, epicardially with respect to heart 16A, or at another location.

Defibrillation lead 18A of FIG. 1A may include an insulative lead body having a proximal end that includes a connector configured to be connected to ICD 10A and a distal portion that includes one or more electrodes. Defibrillation lead 18A may also include one or more conductors that form an electrically conductive path within the lead body and interconnect the electrical connector and respective ones of the electrodes.

Defibrillation lead 18A of FIG. 1A includes a defibrillation electrode that, in the illustrated example, includes two sections or segments 20A and 20B. Segments 20A and 20B are collectively (or alternatively) referred to herein as "defibrillation electrodes 20." Defibrillation electrodes 20 of FIG. 1A are positioned toward the distal portion of defibrillation lead 18A, e.g., toward the portion of defibrillation lead 18A extending along sternum 22 of patient 14. Defibrillation lead 18A of FIG. 1A is placed below and/or along sternum 22 such that a therapy vector between defibrillation electrodes 20A or 20B and a housing electrode formed by ICD 10A or on ICD 10A (or other second electrode of the therapy vector) is substantially across a ventricle of heart 16A. The therapy vector may, in one example, be viewed as a line that extends from a point on defibrillation electrodes 20 (e.g., a center of one of the defibrillation electrode sections 20A or 20B) to a point on the housing electrode of ICD 10A. Each of defibrillation electrodes 20 of FIG. 1A may, in one example, be an elongated coil electrode. In some examples, a defibrillation lead may include more or fewer than the two defibrillation electrodes 20 in the illustrated example of defibrillation lead 18A, such as a single coil defibrillation electrode 20.

Defibrillation lead 18A may also include one or more sensing electrodes, such as sensing electrodes 22A and 22B, located along the distal portion of defibrillation lead 18A. In the example illustrated in FIGS. 1A and 1B, sensing electrodes 22A and 22B are separated from one another by defibrillation electrode 20A. In other examples, however, sensing electrodes 22A and 22B may be both distal of defibrillation electrodes 20, or both proximal of defibrillation electrodes 20. In other examples, defibrillation lead 18A may include a greater number or a fewer number of electrodes at various locations proximal and/or distal to defibrillation electrodes 20. In these and/or other examples, ICD 10A may include one or more electrodes on another lead (not shown in FIGS. 1A-1C).

ICD system 4A may sense electrical signals via one or more sensing vectors that include combinations of electrodes 22A and 22B and the housing electrode of ICD 10A.

For example, ICD 10A may obtain electrical signals that are sensed using a sensing vector between sensing electrodes 22A and 22B, obtain electrical signals sensed using a sensing vector between sensing electrode 22B and the conductive housing electrode of ICD 10A, obtain electrical signals sensed using a sensing vector between sensing electrode 22A and the conductive housing electrode of ICD 10A, or a combination thereof. In some instances, ICD 10A may sense cardiac electrical signals using a sensing vector that includes one of the defibrillation electrode sections 20A and 20B and one of sensing electrodes 22A and 22B or the housing electrode of ICD 10A.

The sensed electrical intrinsic signals include electrical signals that are generated by cardiac muscle and are indicative of depolarizations and repolarizations of heart 16A at various times during the cardiac cycle. Moreover, the sensed electrical intrinsic signals may be indicative of one or more cardiac events with respect to the functioning of heart 16A. The sensed electrical signals may also include electrical signals, e.g., pacing pulses, generated by PD 12A and delivered to heart 16A. ICD 10A analyzes the electrical signals sensed by the one or more sensing vectors to detect tachyarrhythmia, such as ventricular tachycardia or ventricular fibrillation. In response to detecting the tachyarrhythmia, ICD 10A may begin to charge a storage element, such as a bank of one or more capacitors. Upon determining that the storage element is sufficiently charged, ICD 10A may deliver one or more defibrillation pulses to certain chamber(s) of heart 16A via defibrillation electrodes 20 of defibrillation lead 18A, if ICD 10A determines that the tachyarrhythmia is still present.

In the example of FIG. 1A, PD 12A is implanted within the left ventricle of heart 16A, to provide pacing pulses to the left ventricle, e.g., for CRT therapy. While illustrated as being implanted within the left ventricle as an example, it will be appreciated that PD 12A may be implanted at different positions as well. For instance, PD 12A may be implanted epicardially. That is, in accordance with epicardial implantation, PD 12A may be positioned externally to heart 16A, and may be connected via one or more leads or in a leadless fashion to the left ventricle of heart 16A. Further, in some examples, PD 12A or other PDs may be implanted within or externally to other chambers of heart 16A

PD 12A may be constructed to have dimensions so as to fit within the available volume of the left ventricle of heart 16A, and to be attachable to a wall of the left ventricle of heart 16A. A smaller size of PD 12A may also reduce the risk of thrombus forming in heart 16A. PD 12A may leverage sensing capabilities of ICD 10A, and therefore, may not include sensing circuitry, in some examples. As such, PD 12A may utilize a smaller capacity battery than in scenarios where regular sensing for cardiac events is performed.

For example, ICD 10A may be configured to sense electrical activity of heart 16A, such as atrial depolarizations or P-waves, and determine when PD 12A should deliver one or more pacing signals (e.g., pulses) to the left ventricle of heart 16A. ICD 10A may then transmit control signals to PD 12A to provide PD 12A with timing information associated with the pacing pulses that are to be delivered. Upon receiving the control signals from ICD 10A, PD 12A may deliver the pacing signals or pulses according to the timing information indicated by the received control signals. ICD 10A and PD 12A may operate using transmission schedules and communication schedules in order to limit the amount of time that PD 12A operates communication circuitry that receives the control signals in a powered-on state.

In some examples, ICD 10A may also provide pacing signals as part of the CRT therapy using sensing electrodes 22A and/or 22B of defibrillation lead 18A. In other examples, ICD 10A may be coupled to one or more intracardiac leads carrying respective electrodes configured to be disposed within the right atrium and the right ventricle of heart 16A, and deliver pacing pulses via these intracardiac leads as part of the CRT therapy along with PD 12A. In other examples, additional PDs similar to PD 12A may be disposed within the right atrium and/or the right ventricle of heart 16A. Any PD(s) placed within the right atrium and/or right ventricle of heart 16A may be similarly controlled by ICM 10A. Alternatively, one or both of the PDs in the right atrium and/or right ventricle may provide control signals to PD 12A disposed in the left ventricle of heart 16A.

In other examples, PD 12A implanted in the left ventricle and/or a PD implanted in the right ventricle or other heart chamber may be configured to deliver other pacing therapy, such as bradycardia pacing therapy and/or post-shock pacing, to heart 16A. For example, PD 12A or a PD implanted in or on the right ventricle may deliver A-V synchronous bradycardia pacing therapy, timed relative to the atrial depolarization based on control signals received from ICD 10A in accordance with the techniques described herein.

Again, in some examples, PD 12A may not include sensing circuitry. In other examples, PD 12A may be capable of sensing electrical signals using the electrodes carried on the housing of PD 12A. These electrical signals may be electrical signals generated by cardiac muscle and indicative of depolarizations (e.g. a ventricular depolarization or R-wave, or an atrial depolarization or P-wave) and repolarizations (e.g. a ventricular repolarization or T-wave) of heart 16A at various times during the cardiac cycle. PD 12A may analyze the sensed electrical signals to detect tachyarrhythmias, such as ventricular tachycardia or ventricular fibrillation, bradyarrhythmias, or even shocks. In response to detecting these conditions, PD 12A may, e.g., depending on the type of arrhythmia or shock, begin to deliver bradycardia pacing therapy or post-shock pacing, with or without information from another device. In some examples, PD 12A may only detect arrhythmias in response to failing to detect control signals from ICM 10A for a predetermined period of time, or over a predetermined number of communication windows.

Although PD 12A and ICD 10A may be capable of at least one-way communication, PD 12A and ICD system 4A may, in some instances, be configured to operate completely independently of one another. In such a case, PD 12A and ICD system 4A may not be capable of establishing telemetry or other communication sessions with one another to exchange information about sensing and/or therapy using one-way or two-way communication. This independent operation may be intentional, or may be the result of a failure to synchronize transmission and communication schedules or some other error with one or both devices. In such an instance, instead of sharing information, each of PD 12A and ICD system 4A may analyze the data sensed via their respective electrodes to make arrhythmia detection decisions and/or therapy decisions. As such, each device may not have information as whether the other device will detect the arrhythmia, whether or when the other device will provide therapy, and the like.

Figure 2:
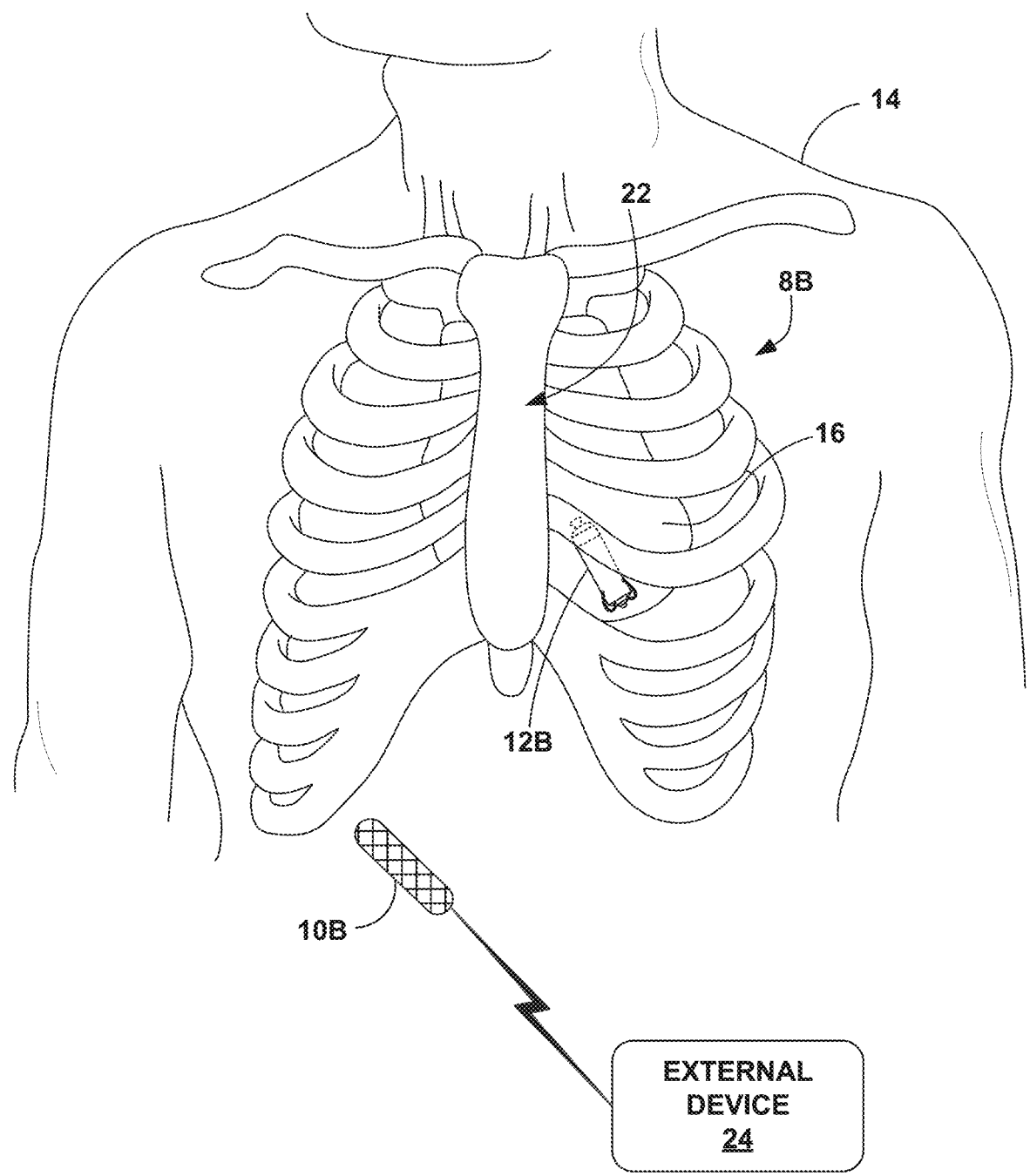
FIG. 2 is a conceptual diagram illustrating is an example front view of a patient implanted with another example medical device system that includes an insertable cardiac monitoring (ICM) device that is inserted subcutaneously or substernally in the patient, and a PD implanted within a cardiac chamber of the patient, in accordance with one or more aspects of this disclosure.

Although FIG. 1A is illustrated and described in the context of a substernal ICD system 4A and a PD 12A, techniques in accordance with one or more aspects of the present disclosure may be applicable to other medical device systems. One example of another medical device system 8 that may implement the techniques of this disclosure for state-based detection of P-waves is shown in FIG. 2 and discussed in further detail below with respect to FIG. 2. In another example, instead of an extravascular ICD system, a subcutaneous or submuscular pacing device coupled to a ventricular intracardiac lead may be implanted within the patient. In this manner, the pacing device may provide pacing pulses to the right ventricle of heart 16A via the intracardiac lead, and also control PD 12A to provide pacing pulses to the left ventricle of heart 16A. As such, the examples of FIGS. 1A-1C and 2 are illustrated for example purposes only, and should not be considered limiting of the techniques described herein, in any way.

External device 24A may be configured to communicate with ICD 10A and/or PD 12A. In examples where external device 24A only communicates with one of ICD 10A or PD 12A, the non-communicative device may receive instructions from or transmit data to the device in communication with external device 24A. In some examples, external device 24A may include, be, or be part of one or more of a handheld computing device, a computer workstation, or a networked computing device. External device 24A may include a user interface that is configured or otherwise operable to receive input from a user. In other examples, external device 24A may process user interactions that are relayed remotely, such as via a networked computing device. External device 24A may process user interactions to enable users to communicate with PD 12A and/or ICD 10A. For example, external device 24A to process user input to send an interrogation request and retrieve therapy delivery data, to update therapy parameters that define therapy, to manage communication between PD 12A and/or ICD 10A, or to perform any other activities with respect to PD 12A and/or ICD 10A. Although the user is typically a physician, technician, surgeon, electrophysiologist, or other healthcare professional, the user may be patient 14 in some examples.

External device 24A may also allow the user to define how PD 12A and/or ICD 10A senses electrical signals (e.g., ECGs), detects arrhythmias (e.g., tachyarrhythmias), delivers therapy, and communicates with other devices of cardiac medical device system 8A. For example, external device 24A may be used to change tachyarrhythmia detection parameters. In another example, external device 24A may be used to manage therapy parameters that define therapies. In examples in which PD 12A and ICD 10A are configured to communicate with each other, external device 24A may be used to alter communication protocols between PD 12A and ICD 10A. For example, external device 24A may instruct PD 12A and/or ICD 10A to switch between one-way and two-way communication and/or change which of PD 12A and/or ICD 10A are tasked with initial detection of arrhythmias.

External device 24A may also allow a user to program A-V and/or V-V delays for CRT therapy. For example, external device 24A may allow a user to select an A-V delay, and program ICD 10A to trigger PD 12A to deliver ventricular pacing pulse at certain time after a detected P-wave based on the selected A-V delay. External device 24A may also be configured to program the parameters used by ICD 10A to detect P-waves according to the techniques described herein, such as a temporal and morphological criteria for the various states of a cardiac cycle. External device 24A may also, or alternatively, be configured to adjust parameters defining communication such as the duration of windows, the rate of windows, rate of synchronization signals, allowable lapses in communication before one or more devices attempt to re-establish communication, and other such parameters.

External device 24A may communicate with PD 12A and/or ICD system 4A via wireless communication using any techniques known in the art. Examples of communication techniques may include, for example, proprietary and non-proprietary radiofrequency (RF) telemetry, inductive telemetry, acoustics, and tissue conduction communication (TCC), but other techniques are also contemplated. During TCC, current is driven through the tissue between two or more electrodes of a transmitting device. The electrical signal spreads and can be detected at a distance by measuring the voltage generated between two electrodes of a receiving device.

PD 12A may be configured to provide CRT or other pacing regimens or even adjust cardiac therapy based on the application of anti-tachyarrhythmia shock therapy by ICD 10A. It may be beneficial for PD 12A to have access to information regarding whether/when ICD 10A has delivered tachyarrhythmia shock therapy to heart 16A. In response to the delivery of the tachyarrhythmia shock therapy, PD 12A may activate post-shock pacing. For instance, ICD 10A may transmit a control signal indicating that a shock is imminent or that PD 12A should begin pacing, such as at a time after the control signal indicated by the control signal.

In some examples, PD 12A and ICD 10A may engage in communication to facilitate the appropriate detection of arrhythmias and/or appropriate delivery of pacing therapy. The communication may include one-way communication in which one device is configured to transmit communication messages and the other device is configured to receive those messages according to the respective schedule. The communication may instead include two-way communication in which each device is configured to transmit and receive communication messages. Both of PD 12A and ICD 10A may be configured to toggle between one-way communication modes and two-way communication modes based on the therapy that patient 14 may need. The communication may be via TCC or other communication signals, e.g., RF communication signals.

In combination with, or as an alternative to, communication between PD 12A and ICD system 4A, PD 12A may be configured to detect an anti-tachyarrhythmia shock delivered by ICD system 4A or by an external defibrillator according to the detection of an electrical signal across two or more electrodes of PD 12A. PD 12A may be configured to detect an anti-tachyarrhythmia shock based on electrical characteristics of the anti-tachyarrhythmia shock. Even though different defibrillation devices may provide different waveforms, including different pulse durations and amplitudes, defibrillation pulses generally have electrical signal characteristics such that detection of an anti-tachyarrhythmia shock can occur even without prior knowledge as to an anti-tachyarrhythmia shock waveform of an implanted or external defibrillator. In this manner, PD 12A may coordinate the delivery of cardiac stimulation therapy, including delivery of post-shock pacing.

In some examples, PD 12A detects the anti-tachyarrhythmia shock by measuring the voltage across the electrode inputs of the implanted device. PD 12A may detect one or more signal characteristics of an anti-tachyarrhythmia shock. The signal characteristics include, but are not limited to, the following: detection of the high amplitude level of an anti-tachyarrhythmia shock, detection of a high slew rate of the leading and trailing edges, and detection of a large post-shock polarization change. Detection of more than one signal characteristic may improve sensitivity and/or specificity. For example, PD 12A may detect a high level of an anti-tachyarrhythmia shock in combination with one or both of the detection of a high slew rate of the leading and trailing edges, and the detection of a large post-shock polarization change.

In response to detection of the anti-tachyarrhythmia shock, the PD 12A may activate post-shock pacing, such as VVI (Ventricular sensing, Ventricular pacing, Inhibited pacing when intrinsic ventricular depolarization sensed) post-shock pacing. Post-shock pacing may be used to provide pacing support if the patient's heart does not begin to beat normally immediately following an anti-tachyarrhythmia shock. PD 12A may deliver post-shock pacing with a higher than normal pulse amplitude and pulse width (relative to typical cardiac pacing) to minimize the risk of loss of capture following an anti-tachyarrhythmia shock. A higher capture threshold may occur as a result of tissue stunning due to elevated current in the myocardial tissue from the anti-tachyarrhythmia shock delivery. A higher threshold may also occur as a result of physiological changes in the tissue resulting from lack of blood flow to the myocardium during ventricular fibrillation (VF). Furthermore, after an anti-tachyarrhythmia shock there can be increased polarization at the electrode-tissue interface resulting in the need for a higher voltage to overcome the polarization.

In one example, PD 12A may deliver post-shock pacing to heart 16A via at least a subset of the set of electrodes of PD 12A. In some examples, PD 12A may deliver the post-shock pacing after entering a post-shock pacing mode in response to detecting the shock. In some examples, PD 12A may use a timer to determine when a predetermined time has elapsed, during which the shock should have been delivered. PD 12A may begin post-shock pacing after the predetermined period has elapsed and/or stop post-shock pacing.

Although ICD 10A and PD 12A may perform coordinated communication in order to provide pacing or CRT, these medical devices may provide other therapies to patient 14 using transmission and communication schedules described herein. For example, ICD 10A may be a subcutaneous, substernal, or transvenous device (although discussed as a substernal device with respect to FIG. 1A) that detects the atrial depolarization (i.e., P-wave) and transmits the control signal telling a leadless pacer in the left ventricle (LV) (e.g., PD 12A) when to deliver a pacing signal in order to add CRT to the functionality of ICD 10A. In another example, any device may be implanted subcutaneously in the torso of patient 14 to detect the atrial depolarization (P-wave) and transmit a control signal to PD 12A in the left ventricle, or PDs in both ventricles, in order to deliver CRT or other forms of ventricular pacing to heart 16A timed to the occurrence of the atrial depolarization.

In another example, two PD devices (e.g., including PD 12A illustrated in FIG. 1A) may be in communication during ventricular pacing with atrial sensing (VDD) with one PD in the right ventricle to detect the P-wave, deliver pacing signals to and sense activity from the right ventricle, and send a TCC or other signal to PD 12A in the left ventricle to deliver a pacing signal to implement atrial synchronous bi-ventricular (bi-V) pacing. This pacing mode may avoid pacing on a T-wave following a PVC because the PD implanted in the right ventricle may provide sensing and also provides backup ventricular pacing and sensing with ventricular event inhibition (VVI) pacing therapy if the TCC signals between the devices are lost.

FIG. 2 is a conceptual diagram illustrating an example front view of patient 14 implanted with another example medical device system that includes an insertable cardiac monitoring (ICM) device 10B that is inserted subcutaneously or substernally in the patient, and PD 12B implanted either epicardially or within a cardiac chamber of patient 14, in accordance with one or more aspects of this disclosure. Components illustrated in FIG. 2 with like numbers those of FIGS. 1A-1C may be similarly configured and may provide similar functionality to the similarly-numbered components illustrated in FIGS. 1A-1C. Medical device system 8B of FIG. 2 may leverage cardiac signal sensing capabilities of ICM 10B to perform one or more of the techniques described herein with respect to P-wave detection. ICM 10B may be configured to detect a P-wave using the techniques of this disclosure, and in turn, drive PD 12B to deliver pacing therapy to heart 16, concurrently or substantially concurrently with the occurrence of a subsequent R-wave in the cardiac cycle. In some examples, ICM 10B may take the form of a Reveal LINQ™ ICM, available from Medtronic plc, of Dublin, Ireland.

Medical device system 8A of FIGS. 1A-1C and medical device system 8B of FIG. 2 may each be configured to perform the P-wave detection and pacing therapy-triggering techniques of this disclosure. As such, the P-wave detection techniques of this disclosure are described hereinafter as being performed generically by "medical device system 8," "implantable medical device (IMD) 10," which may include as examples ICD 10A and ICM 10B, and/or "PD 12," although it will be appreciated that the described techniques may be performed by the respective corresponding systems/devices illustrated in FIGS. 1A-1C or FIG. 2. In accordance with various aspects of this disclosure, medical device system 8 and/or components thereof may be configured to detect a P-wave in the cardiac cycle of heart 16, and deliver pacing therapy prior to, coincident with, or approximately coincident with a subsequent intrinsic R-wave of the cardiac cycle. Medical device system 8 may have access to criteria data for transitioning between various states (e.g., a P-wave, an R-wave, a T-wave, etc.) of a cardiac cycle model. As examples, medical device system 8 may store the state-transition criteria information to one or more memory devices that are included in the components illustrated in FIGS. 1A-1C and 2, and/or to memory device(s) that are otherwise communicatively coupled to one or more of the illustrated components of medical device system 8.

Additionally, medical device system 8 may employ a state-based sequencer and state transition probability information to detect a transition of the cardiac signal into a P-wave state, e.g., prior to the end of the P-wave. By implementing the techniques of this disclosure to detect the P-wave, medical device system 8 may trigger pacing therapy to heart 16A prior to or concurrently with the occurrence of an immediately subsequent R-wave of the cardiac cycle, or substantially coincident with the occurrence of the immediately subsequent R-wave of the cardiac cycle. For instance, medical device system 8 may trigger the pacing such that the pacing may occur prior to when an intrinsic R-wave is expected to occur.

As described above, IMDs 10 may, in various examples, represent different types of cardiac monitoring (and in some cases therapy) devices that can be implanted substernally, subcutaneously, or elsewhere in the body of patient 14. In any of these implementations, IMD 10 includes interface hardware and sensing circuitry that senses a cardiac signal that varies as a function of a cardiac cycle of heart 16. For instance, the sensing circuitry of ICM 10 may detect the timing of cardiac depolarization and/or cardiac contraction events, based on the cardiac signal that varies as a function of the cardiac cycle.

Processing circuitry of IMD 10 may implement one or more techniques of this disclosure to detect a P-wave in the sensed cardiac signal in time to trigger PD 12A to deliver pacing therapy concurrently or approximately concurrently with the immediately following R-wave. The processing circuitry of IMD 10 may compare various characteristics of the cardiac signal to the stored criteria for state transitions. In terms of cardiac signal characteristics to be compared to the stored criteria, the processing circuitry of IMD 10 may use a combination of temporal context and morphological values extrapolated from the cardiac signal sensed by the sensing circuitry of IMD 10 to detect a P-wave in the sensed cardiac signal. One example of temporal context that the processing circuitry of IMD 10 may use is the length of time that has elapsed since the last R-wave detected in the cardiac cycle, as reflected in the cardiac signal sensed by the sensing circuitry of IMD 10.

Figure 7:
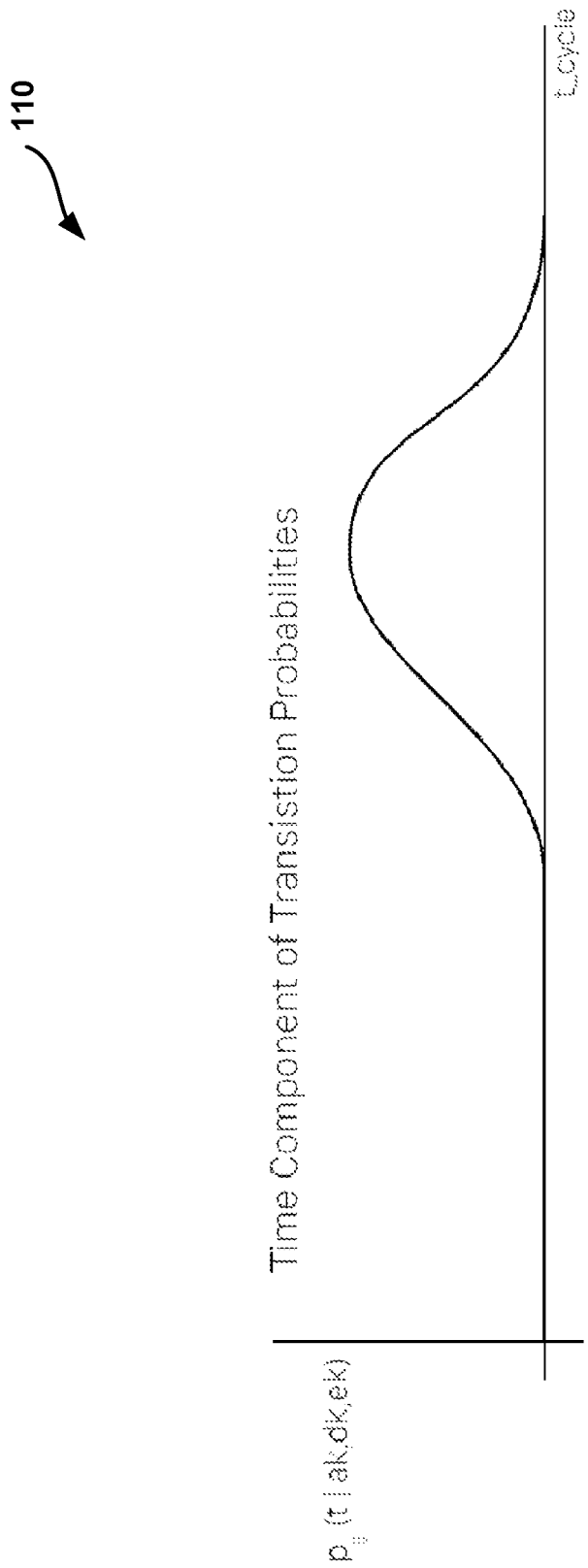
FIG. 7 is a graph illustrating changes in state transition probabilities with time.

The processing circuitry of IMD 10 may compare the elapsed time and the extrapolated morphological values to a set of state transition criteria for each state transition. The state transition criteria for each state transition may include a predetermined time-based probability of the state transition as a function of time from the detected R-wave (an example of which is shown in FIG. 7) and a set of filter transform, e.g., wavelet, coefficients representative of morphological values for corresponding post-R-wave states. Examples of post-R-wave states include, in ascending chronological order, an iso-electric1 state, a T-wave state, an iso-electric2 state, and a P-wave state. The chronological order of post-R-wave states described above remains the same, whether the post-R-wave states follow an occurrence of a normal R-wave state or an ectopic R-wave state. The length of the states may vary, however, from cardiac cycle to cardiac cycle.

According to the techniques of this disclosure, the processing circuitry of IMD 10 may model variations of so-called "typical" cardiac cycles. In some non-limiting examples, the processing circuitry of IMD 10 may use a hidden Markov process to model the typical variations that reflect cardiac cycle events indicating the state transitions of a normal (e.g., expected) cardiac cycle. The processing circuitry of IMD 10 may utilize theoretically-derived criteria as a starting point to determine state transition criteria of the normal cardiac cycle, and may tune the criteria on an ongoing basis, using online learning of probability information. In some non-limiting examples, the processing circuitry of IMD 10 may use Bayesian probabilities to implement the online learning aspects of the fine-tuning techniques described herein.

IMD 10 may periodically sample the cardiac electrogram and, e.g., for each sample, determine the probability of each possible state transition of the post-R-wave path from the current state as a function of cycle time and a morphological evaluation of the cardiac electrogram at that sample. The cycle time may be expressed as the length of time elapsed since the R-wave that was most recently detected by IMD 10, and the time-based component of the probability of each possible state transition determined as a function of the elapsed time since the R-wave, e.g., using a function as shown in FIG. 7. Each possible state transition from the current state may be associated with a respective function of probability over elapsed cycle time.

To determine the morphology-based component of the probability of each state transition from the current state, the processing circuitry of IMD 10 may characterize the morphology of a window of samples of the cardiac electrogram including the current sample, e.g., sample-by-sample with center alignment on a fixed delay=$(½)*(2^N)$. The processing circuitry of IMD 10 may apply a filter transform, such as a Fourier or wavelet transform, to the cardiac electrogram samples and to determine coefficient values, which may be compared to criteria for each possible state transition to determine a morphology-based component of the probability for each state transition. As such, the processing circuitry of IMD 10 may perform a probability-based determination of the present state (other than an R-wave, which is directly detected from the cardiac signal) based on a function input that is a combination of a post-R-wave cycle time and morphology, e.g., a set of wavelet-derived coefficients. In some examples, the processing circuitry of IMD 10 may use the filter transform, e.g., wavelet-derived, coefficients as target filters in the probability-based determination of the present post-R-wave state of the cardiac cycle of heart 16.

Presented below is an equation that generically illustrates one example of a path transition probability for a particular state from the present state in terms of a function that the processing circuitry of IMD 10 may be configured to solve, to determine the present post-R-wave state of the cardiac cycle of heart 16 based on the cardiac signal sensed by the sensing circuitry of IIMD 10:

$$p_{ij}=f(t\_cycle, a_k, d_k, e_k)$$

where:
  t_cycle represents the time elapsed since the last time an R-wave was detected in the cardiac cycle,
  $a_k$ represents one or more discrete wavelet transform (DWT) "average" coefficients, such as Haar wavelet "average" coefficients,
  $d_k$ represents one or more DWT "difference" coefficients, such as Haar wavelet "difference" coefficients,
  $e_k$ represents one or more DWT "difference of difference" coefficients, such as Haar wavelet "difference of difference" coefficients, and
  k represents an integer value in a range of desired bandwidths/scales of the respective Haar wavelet coefficients. In some examples, the range of integer values in which k falls is expressed as a range of 1 to N, with 1 being the lower bound (floor) and 'N' representing the upper bound (ceiling) of the range of desired values. Different bandwidths/scales of coefficients may be, but are not necessarily, considered for different state transitions. Further, some or all of the state transitions may be identified using any one or more average, difference, difference of difference, other possible coefficients. Different coefficients may, in some examples, be more discriminative of different state transitions, and the coefficients used to identify a particular state transition may be selected accordingly. Additionally, as indicated above, Haar wavelet coefficients are but one example of transfer function coefficients that may be determined based on the sampled cardiac electrogram to determine a probability of a particular state transition according to the techniques described herein.

At an initial stage, with no cardiac cycle heuristics or limited cardiac cycle heuristics available with respect to patient 14, the processing circuitry of IMD 10 may use theoretically-derived (a priori) probabilities for each of the post-R-wave states. In turn, the processing circuitry of IMD 10 may tune the a priori probabilities for one or more of the post-R-wave states using patient-specific morphologies gathered via monitoring the cardiac cycle of patient 14. That is, the processing circuitry of IMD 10 may develop heuristics on cardiac cycle state morphologies that are observed with respect to patient 14, and in turn, may apply the heuristics to develop more patient-specific probability information for one or more of the cardiac cycle states for patient 14. For example, processing circuitry of IMD 10 (or an external device) may apply the Haar wavelet or other transform to observed cardiac electrogram morphologies of patient 14 to determine template sets of coefficient values for each state transition.

As discussed above, the processing circuitry of IMD 10 may calculate the transition probability for each post-R-wave state of the cardiac cycle using data that can be classified into two broad categories. That is, the processing circuitry of IMD 10 may use data that falls into a "temporal" category, and data that falls into a "morphological" category. The morphological component of each respective state transition probability may include a set of instantaneous wavelet (or other transform) coefficients associated with a particular point of the cardiac cycle. In examples in which different coefficients are evaluated for different state transitions, the processing circuitry of IMD 10 may calculate a superset of wavelet or other transform coefficients, from which to select particular subsets of coefficients for each of the particular post-R-wave state transitions. The processing circuitry of IMD 10 may calculate a separate superset of wavelet coefficients on a sample-by-sample basis. As discussed above, the processing circuitry of IMD 10 may calculate each such superset of wavelet coefficients corresponding to a single current sample based on a window of samples with a respective center alignment on a fixed delay relative to the current sample that is expressed as $(\frac{1}{2})*(2^N)$, wherein 'N' is the number of samples of the fixed delay, in one example.

The temporal component of each respective state transition probability includes the elapsed time since the most recently-detected R-wave of the cardiac signal. For instance, the processing circuitry of IMD 10 may determine the elapsed time by measuring the length of time that has passed since the detection of the most recently-detected R-wave of the cardiac cycle of patient 14. The temporal component of the state transition probability reflects an expected delay from the last-detected R-wave until the occurrence of the post-R-wave state for which the transition probability is being applied.

Figure 3:
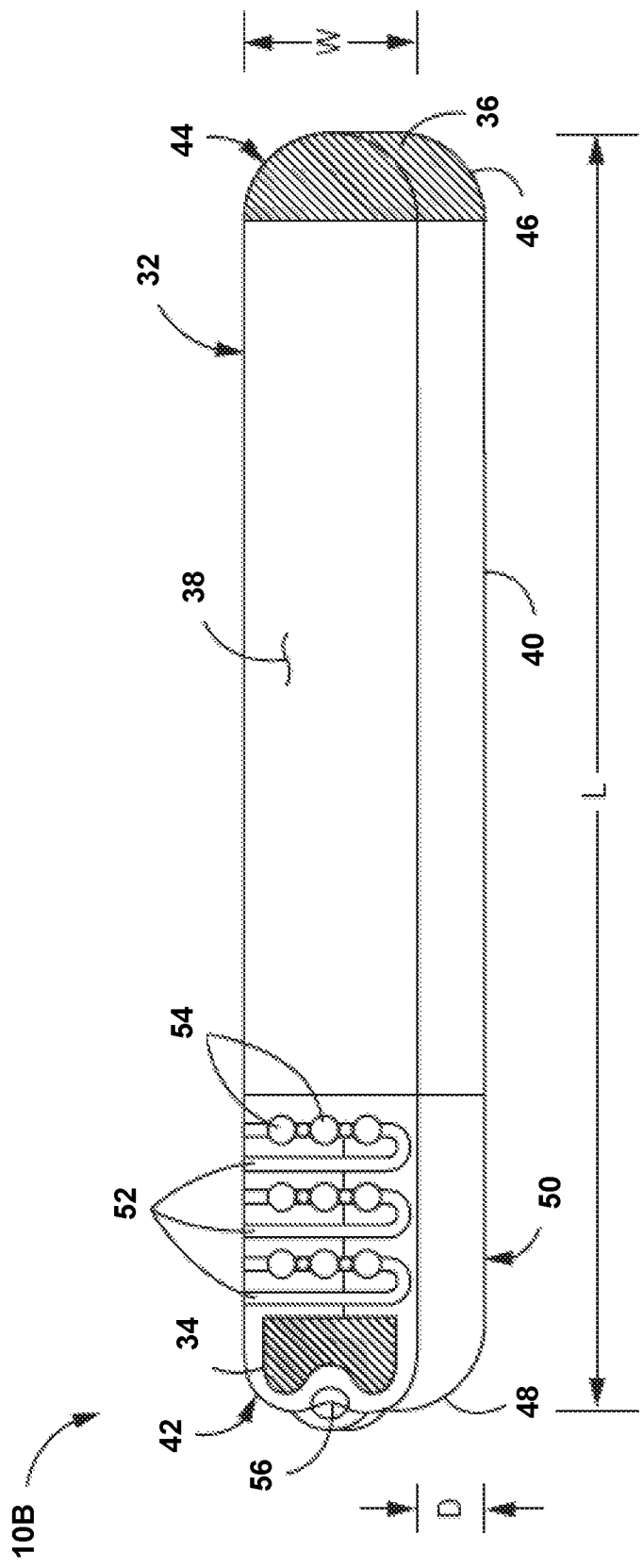
FIG. 3 is a conceptual drawing illustrating an example configuration of the ICM device illustrated in FIG. 2.

FIG. 3 is a conceptual drawing illustrating an example configuration of ICM 10B illustrated in FIG. 2. In the example shown in FIG. 3, ICM 10B may be embodied as a monitoring device having housing 32, proximal electrode 34 and distal electrode 36. Housing 32 may further include first major surface 38, second major surface 40, proximal end 42, and distal end 44. Housing 32 encloses electronic circuitry located inside the ICM 10B and protects the circuitry contained therein from body fluids. Electrical feedthroughs provide electrical connection of electrodes 34 and 36.

In the example shown in FIG. 3, ICM 10B is defined by a length L, a width W and thickness or depth D and is in the form of an elongated rectangular prism wherein the length L is much larger than the width W, which in turn is larger than the depth D. In one example, the geometry of the ICM 10B—in particular a width W greater than the depth D—is selected to allow ICM 10B to be inserted under the skin of the patient using a minimally invasive procedure and to remain in the desired orientation during insertion. For example, the device shown in FIG. 3 includes radial asymmetries (notably, the rectangular shape) along the longitudinal axis that maintains the device in the proper orientation following insertion. For example, in one example the spacing between proximal electrode 34 and distal electrode 36 may range from thirty millimeters (mm) to fifty-five mm, thirty-five mm to fifty-five mm, and from forty mm to fifty-five mm and may be any range or individual spacing from twenty-five mm to sixty mm. In addition, ICM 10B may have a length L that ranges from thirty mm to about seventy mm. In other examples, the length L may range from forty mm to sixty mm, forty-five mm to sixty mm and may be any length or range of lengths between about thirty mm and about seventy mm. In addition, the width W of major surface 38 may range from three mm to ten mm and may be any single or range of widths between three mm and ten mm. The thickness of depth D of ICM 10B may range from two mm to nine mm. In other examples, the depth D of ICM 10B may range from two mm to five mm and may be any single or range of depths from two mm to nine mm. In addition, ICM 10B according to an example of the present disclosure is has a geometry and size designed for ease of implant and patient comfort. Examples of ICM 10B described in this disclosure may have a volume of three cubic centimeters (cm) or less, one-and-a-half cubic cm or less or any volume between three and one-and-a-half cubic centimeters. In addition, in the example shown in FIG. 3, proximal end 42 and distal end 44 are rounded to reduce discomfort and irritation to surrounding tissue once inserted under the skin of the patient. In some examples, ICM 10B, including instrument and method for inserting ICM 10B is configured as described, for example, in U.S. Patent Publication No. 2014/0276928, incorporated herein by reference in its entirety. In some examples, ICM 10B is configured as described, for example, in U.S. Patent Publication No. 2016/0310031, incorporated herein by reference.

In the example shown in FIG. 3, once inserted within the patient, the first major surface 38 faces outward, toward the skin of the patient while the second major surface 40 is located opposite the first major surface 38. Consequently, the first and second major surfaces may face in directions along a sagittal axis of patient 14A (e.g., see FIG. 2), and this orientation may be consistently achieved upon implantation due to the dimensions of ICM 10B. Additionally, an accelerometer, or axis of an accelerometer, may be oriented along the sagittal axis.

Proximal electrode 34 and distal electrode 36 are used to sense cardiac signals, e.g. ECG signals, intra-thoracically or extra-thoracically, which may be sub-muscularly or subcutaneously. ECG signals may be stored in a memory of the ICM 10B, and ECG data may be transmitted via integrated antenna 52 to another medical device, which may be another implantable device or an external device, such as external device 14A. In some example, electrodes 34 and 36 may additionally or alternatively be used for sensing any biopotential signal of interest, which may be, for example, an EGM, electroencephalogram (EEG), electromyogram (EMG), or a nerve signal, from any implanted location.

In the example shown in FIG. 3, proximal electrode 34 is in close proximity to the proximal end 42 and distal electrode 36 is in close proximity to distal end 44. In this example, distal electrode 36 is not limited to a flattened, outward facing surface, but may extend from first major surface 38 around rounded edges 46 and/or end surface 48 and onto the second major surface 40 so that the electrode 36 has a three-dimensional curved configuration. In the example shown in FIG. 3, proximal electrode 34 is located on first major surface 38 and is substantially flat, outward facing. However, in other examples, proximal electrode 34 may utilize the three-dimensional curved configuration illustrated with respect to distal electrode 36 in FIG. 3, providing a three-dimensional proximal electrode. In other examples still, distal electrode 36 may utilize a substantially flat, outward facing electrode located on first major surface 38 similar to that shown in FIG. 3 with respect to proximal electrode 34. The various electrode configurations allow for configurations in which proximal electrode 34 and distal electrode 36 are located on both first major surface 38 and second major surface 40. In other configurations, such as the configuration shown in FIG. 3, only one of proximal electrode 34 or distal electrode 36 is located on both major surfaces 38 and 40. In still other configurations, both proximal electrode 34 and distal electrode 36 are located on one of the first major surface 38 or the second major surface 40 (i.e., proximal electrode 34 may be located on first major surface 38 while distal electrode 36 may be located on second major surface 40). In another example, ICM 10B may include electrodes on both major surface 38 and 40 at or near the proximal and distal ends of the device, such that a total of four electrodes are included on ICM 10B. Electrodes 34 and 36 may be formed of a plurality of different types of biocompatible conductive material, e.g. stainless steel, titanium, platinum, iridium, or alloys thereof, and may utilize one or more coatings such as titanium nitride or fractal titanium nitride.

In the example shown in FIG. 3, proximal end 42 includes a header assembly 50 that includes one or more of proximal electrode 34, integrated antenna 52, anti-migration projections 54, and/or suture hole 56. Integrated antenna 52 is located on the same major surface (i.e., first major surface 38) as proximal electrode 34 and is also included as part of header assembly 50. Integrated antenna 52 allows ICM 10B to transmit and/or receive data. In other examples, integrated antenna 52 may be formed on the opposite major surface as proximal electrode 34, or may be incorporated within the housing 32 of ICM 10B. In the example shown in FIG. 3, anti-migration projections 54 are located adjacent to integrated antenna 52 and protrude away from first major surface 38 to prevent longitudinal movement of the device. In the example shown in FIG. 3 anti-migration projections 54 includes a plurality (e.g., nine) small bumps or protrusions extending away from first major surface 38. As discussed above, in other examples anti-migration projections 54 may be located on the opposite major surface as proximal electrode 34 and/or integrated antenna 52. In addition, in the example shown in FIG. 3 header assembly 50 includes suture hole 56, which provides another means of securing ICM 10B to the patient to prevent movement following insert. In the example shown, suture hole 56 is located adjacent to proximal electrode 34. In one example, header assembly 50 is a molded header assembly made from a polymeric or plastic material, which may be integrated or separable from the main portion of ICM 10B.

Figure 4:
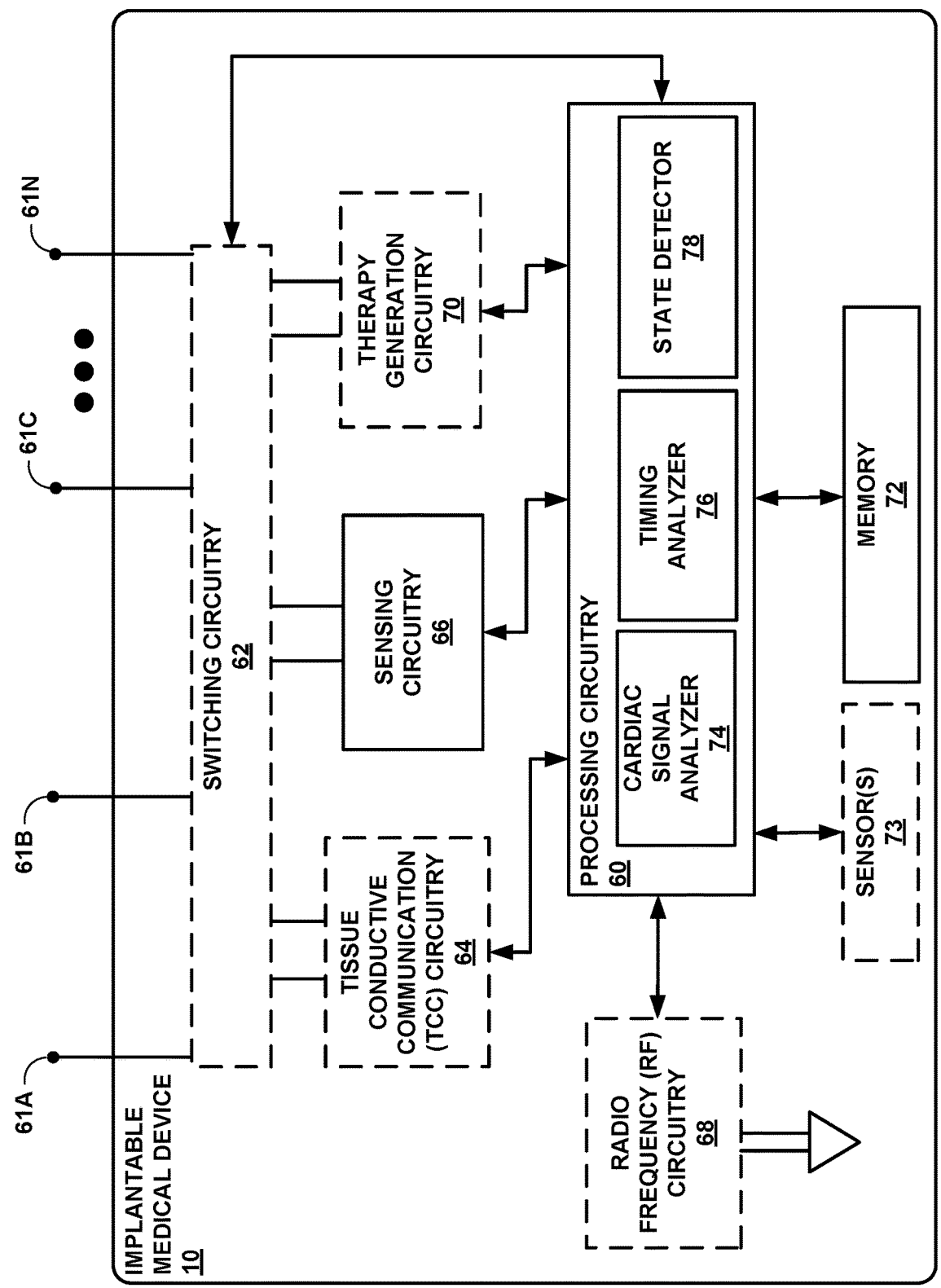
FIG. 4 is a block diagram illustrating details of an example implantable medical device (IMD) configured according to one or more aspects of this disclosure.

FIG. 4 is a block diagram of an example configuration of an IMD 10 that is configured according to one or more aspects of this disclosure. IMD 10 of FIG. 4 may, in various use case scenarios, represent an example of ICD 10A of FIGS. 1A-1C or ICM 10B of FIG. 2. IMD 10 includes two or more electrodes 61A-N (collectively "electrodes 61"), which may correspond to defibrillation electrodes 20 (FIGS. 1A-C), sensing electrodes 22AFIGS. 1A-C), one or more housing electrodes of ICD 10A (FIGS. 1A-C), or electrodes 34 and 36 (FIG. 3).

IMD 10 may include processing circuitry 60 for controlling sensing circuitry 66, (optionally) TCC circuitry 64, (optionally) switching circuitry 62, memory 72, (optionally) RF circuitry 68, (optionally) therapy generation circuitry 70, and (optionally) one or more sensors 73. The optional nature of TCC circuitry 64, switching circuitry 62, RF circuitry 68, therapy generation circuitry 70, and sensor(s) 73 is shown using dashed-line borders to indicate the optional aspect, in FIG. 4. Switching circuitry 62 may include one or more switches, such as metal-oxide-semiconductor field-effect transistors (MOSFETs) or bipolar transistors. Processing circuitry 60 may control switching circuitry 62 to connect electrodes 61 to sensing circuitry 66 to sense a physiological electrical signal, and to TCC circuitry 64 to transmit or receive TCC signals.

Sensing circuitry 66 is configured to receive cardiac electrical signals from selected combinations of two or more electrodes 61, and sense cardiac events attendant to depolarization and repolarization of cardiac tissue. Sensing circuitry 66 may include one or more sensing channels, each of which may be selectively coupled to respective combinations of electrodes 61 to detect electrical activity of a particular chamber of heart 16, e.g., one or more ventricular sensing channels. Each sensing channel may be configured to amplify, filter and rectify the cardiac electrical signal received from selected electrodes coupled to the respective sensing channel to detect cardiac events, e.g., R-waves. For example, each sensing channel may include one or more filters and amplifiers for filtering and amplifying a signal received from a selected pair of electrodes. The resulting cardiac electrical signal may be passed to cardiac event detection circuitry that detects a cardiac event when the cardiac electrical signal crosses a sensing threshold. The cardiac event detection circuitry may include a rectifier, filter and/or amplifier, a sense amplifier, comparator, and/or analog-to-digital converter. Sensing circuitry 66 may output an indication to processing circuitry 60 in response to sensing a cardiac event in a chamber of interest, e.g., an R-wave. In this manner, processing circuitry 60 may receive detected cardiac event signals corresponding to the occurrence of detected R-waves. Indications of detected R-waves may be used by processing circuitry 60 for detecting ventricular arrhythmia episodes, as well as to indicate the start of another cardiac cycle for detection of P-waves according to the techniques described herein. Sensing circuitry 66 may also pass one or more digitized EGM signals to processing circuitry 60 for analysis, e.g., for use in cardiac rhythm discrimination and for morphological analysis to identify state transitions according to the techniques of this disclosure.

TCC circuitry 64 and RF circuitry 68 may each include circuitry for generating and modulating, and in some cases receiving and demodulating, continuous and/or pulsatile communication waveforms. TCC circuitry 64 and RF circuitry 68 may transmit (and in some cases receive) signals via electrodes 61 and an antenna (not shown), respectively.

In some examples, processing circuitry 60 may control switching circuitry 62 to connect electrodes 61 to therapy generation circuitry 70 to deliver a therapy pulse, such as a pacing, cardioversion, or defibrillation pulse to the heart. Therapy generation circuitry 70 is electrically coupleable to electrodes 61, and is configured to generate and deliver electrical therapy to heart 16 via selected combinations of electrodes 61. Therapy generation circuitry 70 may include charging circuitry, and one or more charge storage devices, such as one or more high voltage capacitors and/or one or more low voltage capacitors. Switching circuitry 62 may control when the capacitor(s) are discharged to selected combinations of electrodes 60. Therapy generation circuitry 70 and/or processing circuitry 60 may control the frequency, amplitude, and other characteristics of the therapy pulses. Therapy generation circuitry 70 may deliver the therapy pulses to electrodes 61 when switching circuitry 62 connects therapy generation circuitry 70 to electrodes 61.

Processing circuitry 60 may control switching circuitry 62 by sending control signals to the control terminals of one or more switches of switching circuitry 62. The control signals may control whether the switches of switching circuitry 62 conduct electricity between the load terminals of the switches. If switching circuitry 62 includes MOSFET switches, the control terminals may include gate terminals, and the load terminals may include drain terminals and source terminals.

In the example of FIG. 4, processing circuitry 60 includes several components. It will be appreciated that, in various examples, processing circuitry 60 may include additional components, or alternatively, various functionalities described with respect to two or more of the illustrated components may be shared by a single illustrated component. In the example of FIG. 4, processing circuitry 60 includes cardiac signal analyzer 74, timing analyzer 76, and arrhythmia detector 78.

Processing circuitry 60 may include various types of hardware, including one or more microprocessors, DSPs, ASICs, FPGAs, or any other equivalent integrated or discrete logic circuitry, as well as any combinations of such components. The term "processing circuitry" may generally refer to any of the foregoing logic circuitry, alone or in combination with other logic circuitry, or any other equivalent circuitry. Processing circuitry 60 represents hardware that can be configured to implement firmware and/or software that sets forth one or more of the algorithms described herein. Memory 72 includes computer-readable instructions that, when executed by processing circuitry 60, cause IMD 10 and processing circuitry 60 to perform various functions attributed to IMD 10 and processing circuitry 60 herein. Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

In some examples, processing circuitry 60 may use one or more other physiological parameters, such as a respiration rate exhibited by patient 14, or other physiological parameter(s) that vary autonomically, to adjust one or more aspects of the techniques described herein for detecting P-waves to account for expected autonomic variation in the cardiac cycle and/or waveform. The cardiac cycle length of heart 16 and the timing aspects of the different states of the cardiac cycle may vary based on inputs from the autonomic nervous system of patient 14. For instance, processing circuitry 60 may adjust one or more of the probability function components for each of one or more given state transitions (or all state transitions), such as the temporal component (e.g., probability as a function of time, such as illustrated by the example function of FIG. 7) based on the respiration rate or other autonomically-varying physiological parameter(s) exhibited by patient 14.

In various examples, processing circuitry 60 may use sensor(s) 73 and/or electrodes 61 and sensing circuitry 66 to sense a respiratory signal that varies as a function of a respiratory cycle of patient 14. In some examples, processing circuitry 60 may update (e.g., tune or fine-tune) the state transition criteria (whether the criteria are stored locally or otherwise) based on one or more characteristics of the sensed respiratory signal (such as respiration rate, respiration depth, or variability of these) to obtain a modulated value of the temporal state transition criteria. Referring to FIG. 7, processing circuitry 60 may change the total length of time represented by the probability/time function in correspondence to changes in the respiratory cycle length, and/or change the size and shape of the peak of the function in FIG. 7 based on changes in respiratory cycle length.

Sensor(s) 73 may include, be, or be part of various types of sensing hardware, including, but not limited to, an accelerometer, a pressure sensor, an optical sensor, or a chemical sensor, each of which may be configured to generate a signal that varies as a function of patient respiration or another autonomically varying patient parameter. In some examples where processor 60 uses sensor(s) 73 detect respiration rate information, sensor(s) may include an accelerometer and/or a pressure sensor. In other examples, processor 60 may detect the respiration rate information via changes in impedance of the thorax of patient 14 as indicated by an impedance signal generated by sensing circuitry 66 via electrodes 61. More specifically, with respect to thoracic impedance detection, signal is injected across two of electrodes 61, and processing circuitry 60 may calculate the impedance using the signal information received from electrodes 61 and sensing circuitry 66. The impedance varies over time with the respiration of patient 14, and thus, processing circuitry 60 may detect the respiration signal and thereby determine the respiration rate of patient 14.

Figure 5:
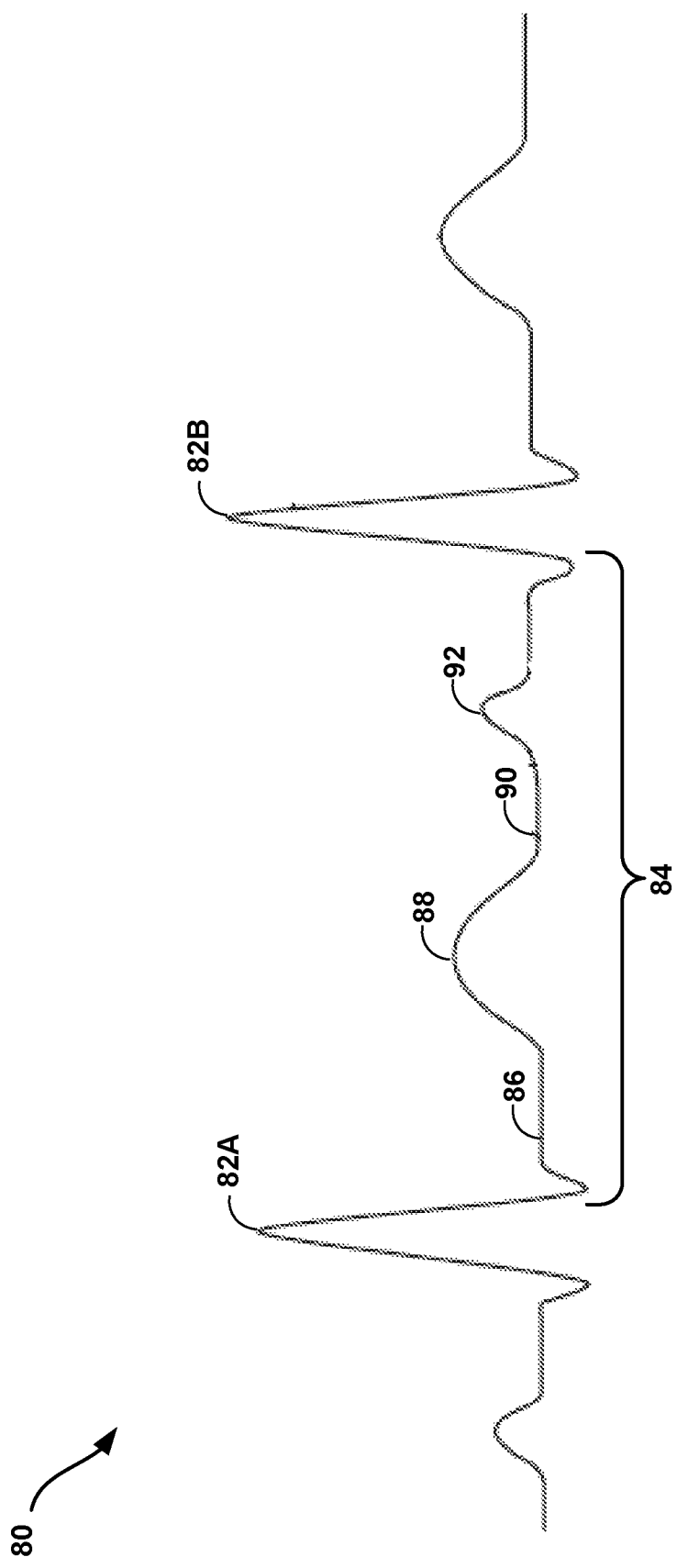
FIG. 5 is a conceptual diagram illustrating portion of an example electrocardiogram that may be analyzed by one or more systems configured according to this disclosure to detect P-waves using the techniques described herein.

FIG. 5 is a conceptual diagram illustrating a portion of an electrocardiogram 80, which is an example of a cardiac electrogram signal that sensing circuitry 66 and processing circuitry 60 may analyze to perform P-wave detection according to the system configurations described herein. Sensing circuitry 66 may provide various types of data outputs to processing circuitry 60, such as data indicating when an R-wave occurs, e.g., in response to the cardiac signal waveform crossing an R-wave detection threshold, as described above. Additionally, sensing circuitry 66 may provide, as an output to processing circuitry 60, a digitized wave form representing the cardiac signal sensed from heart 16A.

Cardiac signal analyzer 74 of processing circuitry 60 may be configured to derive or calculate morphological values from the cardiac signal that sensing circuitry 66 detects using electrodes 61. Cardiac signal analyzer 74 may determine morphological values exhibited by the cardiac signal of patient 14A, at various stages of the cardiac signal. In some examples, sensing circuitry 66 may detect first R-wave 82A from electrocardiogram 80. In some examples, sensing circuitry 66 may detect first R-wave 82A based on a comparison of the amplitude of signal 80 to one or more thresholds, which may be adjustable, according to any of a variety of R-wave detection techniques known in the art. In turn, sensing circuitry 66 may send a communication, referred to herein as an "R-event" signal, to processing circuitry 60. In this way, sensing circuitry 66 may provide processing circuitry 60 an indication of the occurrence (e.g., a start time or a threshold-crossing time) of the R-wave of the sensed cardiac signal.

Cardiac signal analyzer 74 may use the R-event signal to discern the location of an R-wave in the digitized cardiac signal waveform received from sensing circuitry 66. In turn, cardiac signal analyzer 74 may use the R-wave identified by the R-event signal as a starting point from which to detect other states of the cardiac signal, according to the techniques of this disclosure. Additional states that cardiac signal analyzer 74 may detect from electrocardiogram 80 include a noise state and/or a U-wave state. As used in this context, "noise" represents data that cannot otherwise be filtered out of the data sensed by sensing circuitry 66 (e.g., muscle noise having frequencies that overlap with the frequencies of interest). Noise may be detected according to various techniques, such as one or more techniques that call a muscle noise pulse counter that counts a number of peaks in a period of time (e.g., a predetermined number of seconds), and compares the number of peaks in unit time to a threshold. According to some techniques, a count of zero crossings and/or a measure of pulse widths may be used in thresholding-based noise detection. A U-wave represents a relatively small waveform following a T-wave state. The smaller waveform associated with the U-wave state is occasionally present in the cardiac waveform, but is not often present in the cardiac signal waveform. The U-wave waveform can be differentiated from P-waves based on various characteristics, such as timing (e.g., proximity to T-wave and/or based on heart rate), and/or based on waveform morphology.

Additionally, an ectopic beat may have a retrograde P-wave. Retrograde P-waves may or may not be present in a given cardiac signal waveform, and represent conduction from the ventricles to the atria that results in atrial depolarization. As such, retrograde P-waves result in reverse-direction depolarization. Retrograde P-wave depolarizations may be differentiated based on timing information (e.g., elapsed time since the prior R-wave or T-wave), and/or waveform morphology. Triggering ventricular pacing after a retrograde P-wave is typically undesirable, and thus, if cardiac signal analyzer 74 determines that an R-wave is possibly ectopic, then cardiac signal analyzer 74 may delay triggering ventricular pacing until at least the search for the next T-wave or until after a suitable time interval based on the current ventricular rate (e.g., 400 ms). Cardiac signal analyzer 74 may also monitor electrocardiogram 80 after a P-wave for an isoelectric state, such as by comparing a combination of time and morphology-based characteristics, e.g., wavelet coefficients, of a post-P-wave segment of the cardiac signal waveform to criteria for the state transition, such as a cardiac cycle time function and template morphological values for the post-P-wave isoelectric state. If cardiac signal analyzer 74 determines that an intrinsic R-wave occurs before the next ventricular pacing (or "Vpace"), then cardiac signal analyzer 74 may adjust the atrioventricular (AV) delay.

According to various aspects of this disclosure, the components of processing circuitry 60 illustrated in FIG. 4 may be configured to analyze post-R-wave segment 84 of electrocardiogram 80 to predictively determine the occurrence of a P-wave. Upon determining that first R-wave 82A has been detected (e.g., based on an explicit R-wave detection indication received from sensing circuitry 66), processing circuitry 60 may begin analyzing the cardiac signal as having entered post-R-wave segment 84. To analyze post-R-wave segment 84 according to the aspects of this disclosure, cardiac signal analyzer 74 may iteratively (e.g., on a sample-by-sample or other periodic basis) determine a current sample of electrocardiogram 80, and a window or frame of samples of electrocardiogram 80 that includes the current sample. The window or frame of samples of electrocardiogram 80 may be expressed as a length of time, or as a number of samples, e.g., as described above. Cardiac signal analyzer 74 may then determine wavelet or other filter function coefficients, or other morphological measures, for the windowed samples of electrocardiogram 80.

Cardiac signal analyzer 74 may provide the determined coefficients to state detector 78 to be used as inputs to a criteria-matching or criteria-comparison scheme, in accordance with the predictive P-wave detection techniques of this disclosure. Additionally, timing analyzer 76 of processing circuitry 60 may determine the elapsed time since detection of the R-wave, or t_cycle, for the current sample of electrocardiogram 80. In turn, timing analyzer 76 may provide the elapsed times to state detector 78 to be used as an input to a criteria-matching scheme, in accordance with the predictive P-wave detection techniques of this disclosure.

State detector 78 of processing circuitry 60 may perform criteria matching for each current sample, using the wavelet coefficients or other morphological information received from cardiac signal analyzer 74 and the elapsed time received from timing analyzer 76 as inputs to a criteria-matching scheme or criteria-comparison scheme. As discussed above, one non-limiting example of morphological information that may be determined for a particular window of samples of electrocardiogram 80 are wavelet coefficients, e.g., Haar wavelet coefficients. State detector 78 and/or cardiac signal analyzer 74 may group the wavelet coefficients into several categories. One category is denoted herein as "at" and represents Haar wavelet "average" coefficients. For instance, the Haar wavelet average coefficients denoted by $a_k$ may represent an average (e.g., mean, median, or mode) value of the wavelet coefficients for a particular (e.g., "present") frame of electrocardiogram 80.

Another category is denoted herein as "$d_k$," and represents Haar wavelet "difference" coefficients. For instance, the Haar wavelet difference coefficients denoted by $d_k$ may represent a first derivative between the wavelet coefficients of the present frame of electrocardiogram 80 and a previous frame of electrocardiogram 80. Another category is denoted herein as "$e_k$," and represents Haar wavelet "difference of difference" coefficients. For instance, the Haar wavelet difference coefficients denoted by $e_k$ may represent a second derivative between the wavelet coefficients of the present frame of electrocardiogram 80 and a previous frame of electrocardiogram 80. In each instance above, the subscripted letter k represents an integer value that falls within a predetermined range of desired bandwidths/scales of the respective Haar wavelet coefficients. As described above, the range of integer values in which k falls is expressed as a range of 1 to N, with 1 being the lower bound (floor) and 'N' representing the upper bound (ceiling) of the range of desired values. In various non-limiting examples, 'N' may have a value of sixteen (16). In various non-limiting examples, 'N' represents a power of 2, and so 'N' may also have values such as eight (8), thirty-two (32), etc.

In addition to the various categories of wavelet coefficients (in one example, Haar wavelet coefficients) described above, state detector 78 may also use the elapsed time information received from timing analyzer 76 as an input in the criteria-matching scheme. Using the combination the wavelet or other filter function coefficients and the corresponding elapsed time measurement as inputs in a criteria-comparing operation, state detector 78 may determine in which post-R-wave state electrocardiogram 80 most likely is at the measured elapsed time.

In the illustrated example, post-R-wave segment 84 includes four states. The four states are first iso-electric state 86, T-wave state 88, second iso-electric state 90, and P-wave state 92. State detector 78 may use predetermined characteristics taken from "normal" cardiac signals as criteria to identify each of the four states of post-R-wave segment 84. For instance, state detector 78 may use a combination of temporal and morphological characteristics of each post-R-wave state to identify each post-R-wave state.

An example of a temporal characteristic is an elapsed time from an R-wave to the respective post-R-wave state in the normal cardiac signal(s). Elapsed times from an R-wave to the respective post-R-wave state for normal cardiac cycles, e.g., of the patient or representative patient(s), may be used to determine, for each post-R-wave state, the probability of the particular state as a function of the elapsed time. The probability as a function of time for a particular post-R-wave state may be represented graphically as a curve with a maximal probability peak at the most likely time within the cardiac cycle that the particular post-R-wave state would occur, e.g., as illustrated in FIG. 7

Examples of morphological characteristics used as criteria for distinguishing between post-R-wave states include coefficients resulting from application of a filter function, such as a Haar or other wavelet, to normal cardiac signals, e.g., of the patient or representative patient(s). Example coefficients include Haar wavelet average coefficients, Haar wavelet difference coefficients, and Haar wavelet difference-of-difference coefficients associated with each post-R-wave state that is confirmed from a previously-analyzed normal cardiac signal. Each post-R-wave state may be associated with detection criteria that includes, for example, a probability as a function of a time and value(s) of one or more morphological coefficients.

With respect to application of the techniques of this disclosure to identify as P-wave state 92 after R-wave state 82A of the cardiac signal represented by electrocardiogram 80, state detector 78 may apply each elapsed time measurement received from timing analyzer 76 to the probability function for each possible state transition from the current state. State detector 80 may further compare the morphological information of the frame of samples corresponding to the elapsed time measurement, e.g., the corresponding 3-tuple of Haar wavelet coefficients ($a_k$, $d_k$, and $e_k$), generated by cardiac signal analyzer 74 to the template morphological information for each possible state. For each of the states, the comparison may result in a difference or other distance metric between current morphological coefficients and the template coefficients for that state. State detector 78 may determine a probability of the particular post-R-wave state based on a combination, e.g., sum, average, or other combination, of a probability indicated by the current elapsed time and a probability indicated by the distance metric.

As described above, the state transition probability for a particular state from a current state may be generically represented by the mathematical expression $p_{ij}=f(t\_cycle, a_k, d_k, e_k)$. The subscript "ij" of the probability is a generic representation of the pre-transition (or current) and post-transition states of the specific state transition that is currently being assessed. Numerical representations of the "ij" subscript are discussed in further detail below, with respect to FIG. 6. If the t_cycle value received from timing analyzer 76 is the shortest of the candidate time lengths, and/or if the ($a_k$, $d_k$, $e_k$) 3-tuple is within a predetermined acceptable distance of the corresponding ($a_k$, $d_k$, $e_k$) 3-tuple for a normal cardiac signal's iso-electric1 state, then state detector 78 may determine that the cardiac signal of electrocardiogram is in first iso-electric state 86. If the t_cycle value received from timing analyzer 76 is the second-shortest of the candidate time lengths, and/or if the ($a_k$, $d_k$, $e_k$) 3-tuple is within a predetermined acceptable distance of the corresponding ($a_k$, $d_k$, $e_k$) 3-tuple for a normal cardiac signal's T-wave state, then state detector 78 may determine that the cardiac signal of electrocardiogram is in T-wave state 88. If the t_cycle value received from timing analyzer 76 is the second-longest of the candidate time lengths, and/or if the ($a_k$, $d_k$, $e_k$) 3-tuple is within a predetermined acceptable distance of the corresponding ($a_k$, $d_k$, $e_k$) 3-tuple for a normal cardiac signal's iso-electric2 state, then state detector 78 may determine that the cardiac signal of electrocardiogram is in second iso-electric state 90.

If the t_cycle value received from timing analyzer 76 is the longest of the candidate time lengths, and/or if the ($a_k$, $d_k$, $e_k$) 3-tuple is within a predetermined acceptable distance of the corresponding ($a_k$, $d_k$, $e_k$) 3-tuple for a normal cardiac signal's P-wave state, then state detector 78 may determine that the cardiac signal of electrocardiogram is in P-wave state 92. In this way, the various components of IMD 10 may operate collaboratively to detect that the cardiac signal of patient 14, as represented by electrocardiogram 80, is in P-wave state 92. That is, IMD 10 may implement the techniques of this disclosure to detect the occurrence of P-wave state 92 in the cardiac cycle of patient 14 in a predictive manner. For instance, IMD 10 may implement the above-described techniques to use state-based sequencing of the cardiac cycle of patient 14 to detect P-wave state 92 before P-wave state 92 concludes. In this way, in implementations in which IMD 10 is in communication with a PD 12, processing circuitry 60 may trigger TCC circuitry 64 to deliver a signal to PD 12 to deliver ventricular pacing in response to the detection of the P-wave state 92, so that PD 12 may deliver the pacing pulse in conjunction with subsequent or second R-wave state 82B.

State detector 78 may detect that the cardiac signal of patient 14A has entered second R-wave state 82B. More specifically, state detector 78 may detect second R-wave state 82B based on data received from sensing circuitry 66 in the same manner as R-wave state 82A was detected. If state detector 78 determines that state detector 78 had not detected P-wave state 92 before sensing circuitry 66 communicates the detection of second R-wave state 82B, then state detector 78 may determine that P-wave state 92 was missed, from a cardiac signal analysis standpoint. In the case of state detector 78 missing (e.g., failing to detect) P-wave state 92, state detector 78 may tune the probability criteria used for state detection during post-R-wave segment 84. For instance, state detector 78 may tune or adjust the probability criteria only if state detector 78 determines that second R-wave state 82B corresponds to a normal (e.g. not ectopic) R-wave. For instance, state detector 78 may determine that second R-wave state 82B is normal, based on the detection of one or more of iso-electric1 state 86, T-wave state 88, iso-electric2 state 90, or P-wave state 92 between first R-wave state 82A and second R-wave state 82B.

As one example, state detector 78 may change, e.g., reduce the length of, the state transition probability function, e.g., threshold or range of probabilities illustrated in FIG. 7, for classifying the waveform of electrocardiogram 80. Thus, IMD 10 may implement machine learning to tune or retrain the predictive P-wave detection techniques of this disclosure. In this manner, IMD 10 may implement the predictive P-wave detection techniques of this disclosure to accommodate and account for individual patient variations in terms of cardiac cycle characteristics.

In sum, state detector 78 may use information of an R-event signal received from sensing circuitry 66 to perform thresholding-based techniques of this disclosure to detect various post-R-wave states of the cardiac signal represented by the digitized waveform shown in electrocardiogram 80. For instance, state detector 78 may form a respective value profile using state-specific values for the 3-tuple of wavelet coefficients ($a_k$, $d_k$, and $e_k$) for each of iso-electric1 state 86, T-wave state 88, iso-electric2 state 90, or P-wave state 92. That is, each respective value profile includes one or more of a respective set of $a_k$ wavelet coefficients, a respective set of $d_k$ wavelet coefficients, or a respective set of $e_k$ wavelet coefficients. Based on the time elapsed since the last R-wave indicated by the received R-event signal, state detector 78 may compare the wavelet coefficients-based value profile at the presently-analyzed portion of the waveform to the respective value profile (e.g., set or sets of wavelet coefficients) for the post-R-wave state associated with the temporal value indicated by the elapsed time.

Figure 6:
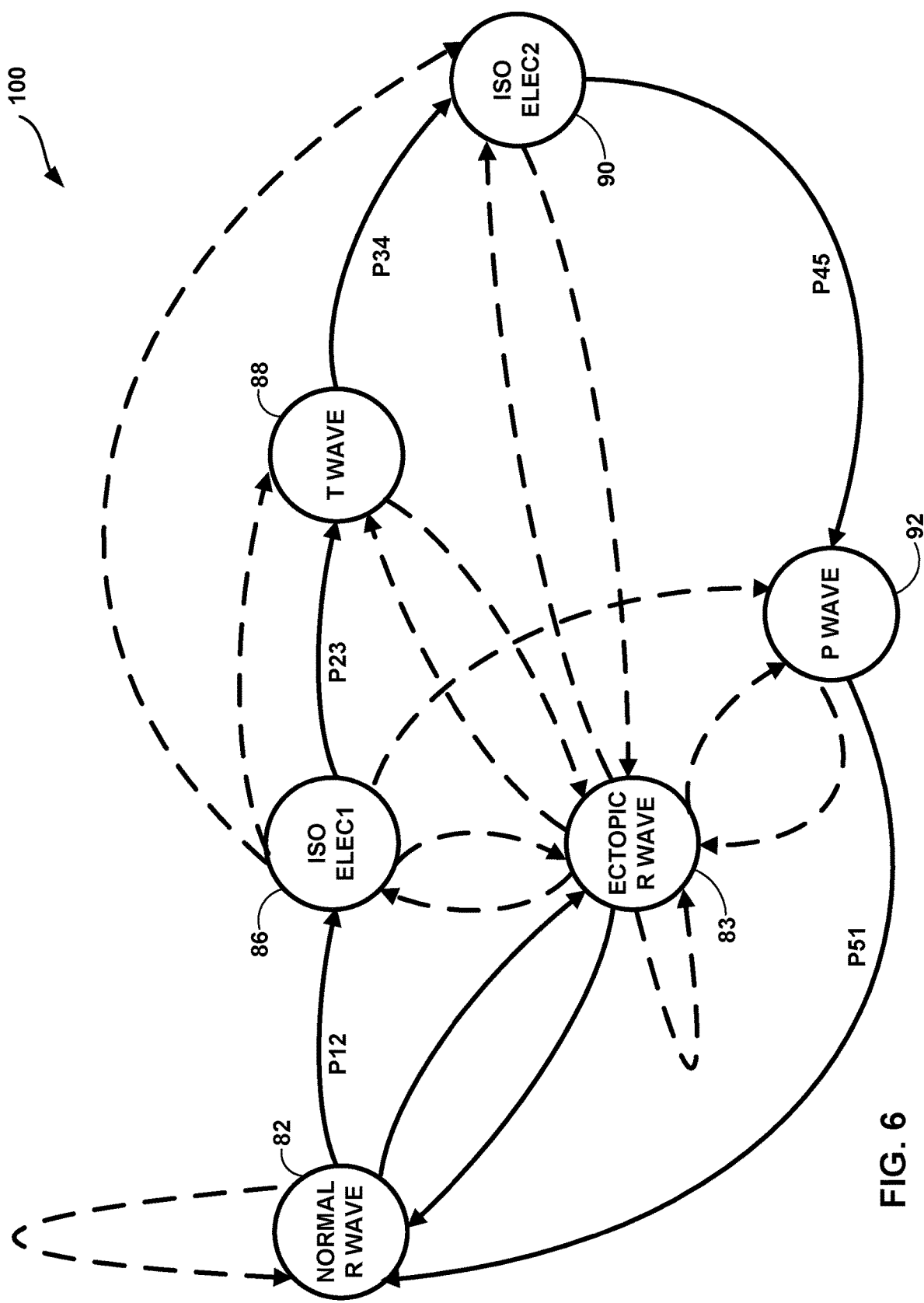
FIG. 6 is a state diagram illustrating a state transition sequence of a sensed cardiac cycle of the patient, which systems of this disclosure may use in accordance with one or more aspects of this disclosure.

FIG. 6 is a state diagram 100 illustrating a state transition sequence of a sensed cardiac cycle of patient 14A, which IMD 10 may use in accordance with one or more aspects of this disclosure. State diagram 100 includes cardiac cycle states that are numbered similarly with respect to the cardiac cycle states illustrated in FIG. 5. State detector 78 may determine a transition probability (denoted generically as "p") with respect to each state illustrated in state diagram 100. For instance, the probability of transitioning from the first state to the second state (e.g., from one of R-wave state 82 or ectopic R-wave state 83 to iso-electricl state 86) is denoted as $p_{12}$. The probability of transitioning from the second state to the third state (e.g., from iso-electricl state 86 to T-wave state 88) is denoted as $p_{23}$. The probability of transitioning from the third state to the fourth state (e.g., from T-wave state 88 to iso-electric2 state 90) is denoted as $p_{34}$. The probability of transitioning from the fourth state to the fifth state (e.g., from iso-electric2 state 90 to P-wave state 92) is denoted as $p_{45}$. The probability of transitioning from the fifth state to the first state (e.g., from P-wave state 92 to R-wave state 82) is denoted as $p_{51}$.

The dashed-line paths in state diagram 100 indicate abnormal state transitions that may possibly occur in a cardiac cycle of patient 14A. As shown in FIG. 6, all transitions into ectopic R-wave state 83 are considered abnormal. For instance, ectopic R-wave state may indicate a premature ventricular contraction of heart 16A. Any movement between the two possible R-wave states of state diagram 100 is considered a normal movement (as shown by the solid-line path), but does not represent a "state transition" as shown by the absence of any $p_{ij}$ label.

As described above, state detector 78 may detect either of R-wave state 82 or ectopic R-wave state 83 based on data communicated by sensing circuitry 66. However, state detector 78 may detect a transition into any of the non-R-wave states of state diagram 100 using the probability-based prediction techniques of this disclosure. That is, state detector 78 may analyze each of transition probabilities $p_{12}$, $p_{23}$, $p_{34}$, and $p_{45}$ using criteria-matching expressed by the mathematical expression $p_{ij}=f(t\_cycle, a_k, d_k, e_k)$. The subscript "ij" of the probability is a generic representation of the pre-transition and post-transition states of the specific state transition that is currently being assessed. That is, in the example of state diagram 100, the term "$p_{ij}$" represents one of transition probabilities transitions $p_{12}$, $p_{23}$, $p_{34}$, or $p_{45}$. State detector 78 may compare the current probability of a particular state transition, determined as discussed above, to a threshold probability, which may be the same or vary between different state transitions. State detector 78 may detect the state transition when the current probability meets and/or exceeds the threshold.

If state detector 78 receives an indication from sensing circuitry 66 that the cardiac signal has entered R-wave state 82 before state detector 78 matches transition probability $p_{34}$ into P-wave state 92, then state detector 78 may determine that P-wave state 92 was missed in the previous iteration of the predictive P-wave detection techniques of this disclosure. In this case, state detector 78 may tune the transition criteria (e.g., the t_cycle function and/or one or more of the Haar wavelet categories) for the non-R-wave states of state diagram 100. If state detector 78 determines that the cardiac signal has entered ectopic R-wave state 83 before state detector 78 matches transition probability $p_{45}$ into P-wave state 92, then state detector 78 may disregard any P-wave-based determination, because P-wave state 92 may or may not have occurred, and therefore may or may not have been missed. By tuning the criteria for detecting the non-R-wave states, and particularly for predictively detecting a transition into P-wave state 92, state detector 78 may implement machine-learning to more accurately detect P-wave state 92 of a subsequent cardiac cycle of patient 14A. By more accurately detecting P-wave state 92, state detector 78 may enable IMD 10 (in cases where IMD 10 includes therapy generation circuitry 70) to deliver pacing therapy via defibrillation electrodes 20, in conjunction with or closer temporal proximity to the atrial contraction of heart 16A that is associated with P-wave state 92.

According to some implementations, identifying the T-wave state 88 may assist state detector 78 to isolate the location of P-wave state 92. That is, the T-wave state 88 may give state detector 78 a second time from which to measure the location of P-wave state 92. In some examples, as discussed above, state detector may implement a second state transition probability function that corresponds to a TP interval and that may begin upon detection of the T-wave state 88. In this, way state detector 78 may use the timing of T-wave state 88 to add a second time reference for a P-wave detecting function for the time elapsed since the peak represented by T-wave state 88, which may improve the ability of state detector 78 to detect the P-wave state 92.

While certain transitions are illustrated in FIG. 6 for purposes of illustration, it will be appreciated that, from a detection standpoint, direct transitions are possible from each state to every other state. That is, missing waveforms may cause state detector 78 to detect direct transitions from an illustrated state to any other illustrated state, whether such a direct state transition is physically possible or not, according to the order shown in FIG. 6. Some such transition detections may be atypical or rare, but may occur due to a variety of reasons, such as oversening or undersensing either from the respective wavelet coefficients, or from a timer (e.g., a so-called "watchdog" timer), or an R-wave sensor reset that restores IMD 10 or components thereof to preset conditions. The time course of the probabilities of such atypical transitions may be different for each transition out of a given state, depending on the particular destination state. For instance, the probabilities of a transition from ectopic R-wave state 83 into second isoelectric state 90 and/or a transition from first isoelectric state 86 into second isoelectric state 90 may be considered to be low, but increasing with time, due to the low probabilities of these transitions.

Additionally, state detector may detect states not illustrated in FIG. 6. In some cases, state detector 78 may detect a P-wave-on-T-wave state, which may occur at increased sinus rates or due to premature atrial contractions (PACs). Described with respect to FIG. 6, such a P-wave-on-T-wave state would replace T-wave state 88, second iso-electric state 90, and P-wave state 92.

FIG. 7 is a graph 110 illustrating changes in state transition probability (the vertical axis or y-axis) with time (the horizontal axis or x-axis). Graph 110 generally follows a bell-curve or Gaussian distribution. State detector 78 may estimate the probabilities for each cardiac cycle state as multi-valued windows ranging from [0.0, 1.0] to [0.0, 1/R, 2/R, . . . R/r] with the center falling at t_center (e.g., a mean or median of the t_cycle range) and where t_width represents the width of the t_cycle range.

State detector 78 may use 0.0 or 1.0 probability values to drive the detection of R-wave state 82 and/or ectopic R-wave state 83. That is, sensing circuitry 66 may either detect or not detect either of R-wave states in the manner discussed above. To distinguish between (normal) R-wave state 82 or ectopic R-wave state 83, state detector 78 may use the t_cycle value at the time of the occurrence of the respective state (either R-wave state 82 or ectopic R-wave state 83).

State detector 78 may analyze the morphological component (e.g. the Haar wavelet coefficients) on a sample-by-sample basis, with respect to electrocardiogram 80. In analyzing the Haar wavelet coefficients plotted on the y-axis of graph 110, state detector 78 may assign a center alignment of the coefficients using a fixed delay. The fixed delay may be expressed by the mathematical expression $((\frac{1}{2})*(2^N))$ where 'N' represents the number of samples of the fixed delay, in one example. State detector 78 may implement various algorithms for selecting state transitions. That is, state detector 78 may implement any of these algorithms to choose a particular state transition at a point of time, given a set of transition probabilities out of the current state. One example of an algorithm that state detector 78 may use is referred to as the "softmax" algorithm.

The state transition probability functions may vary with the current moving average of the RR interval, which may vary due to, for example, exertion such as exercise). The state transition probability functions can also vary based on respiration rate and/or any variability in RP or RR intervals observed in the immediate past. In some examples, state detector 78 may detect a given P-wave using two (2) observed cycle lengths. One of the two cycle lengths may correspond to an RP interval, e.g., begin at a detected R-wave, and the other cycle length may correspond to a TP interval, e.g., begin at a detected T-wave. By using two cycle lengths for P-wave detection, state detector 78 may implement the techniques of this disclosure to increase accuracy in P-wave detection.

Figure 8:
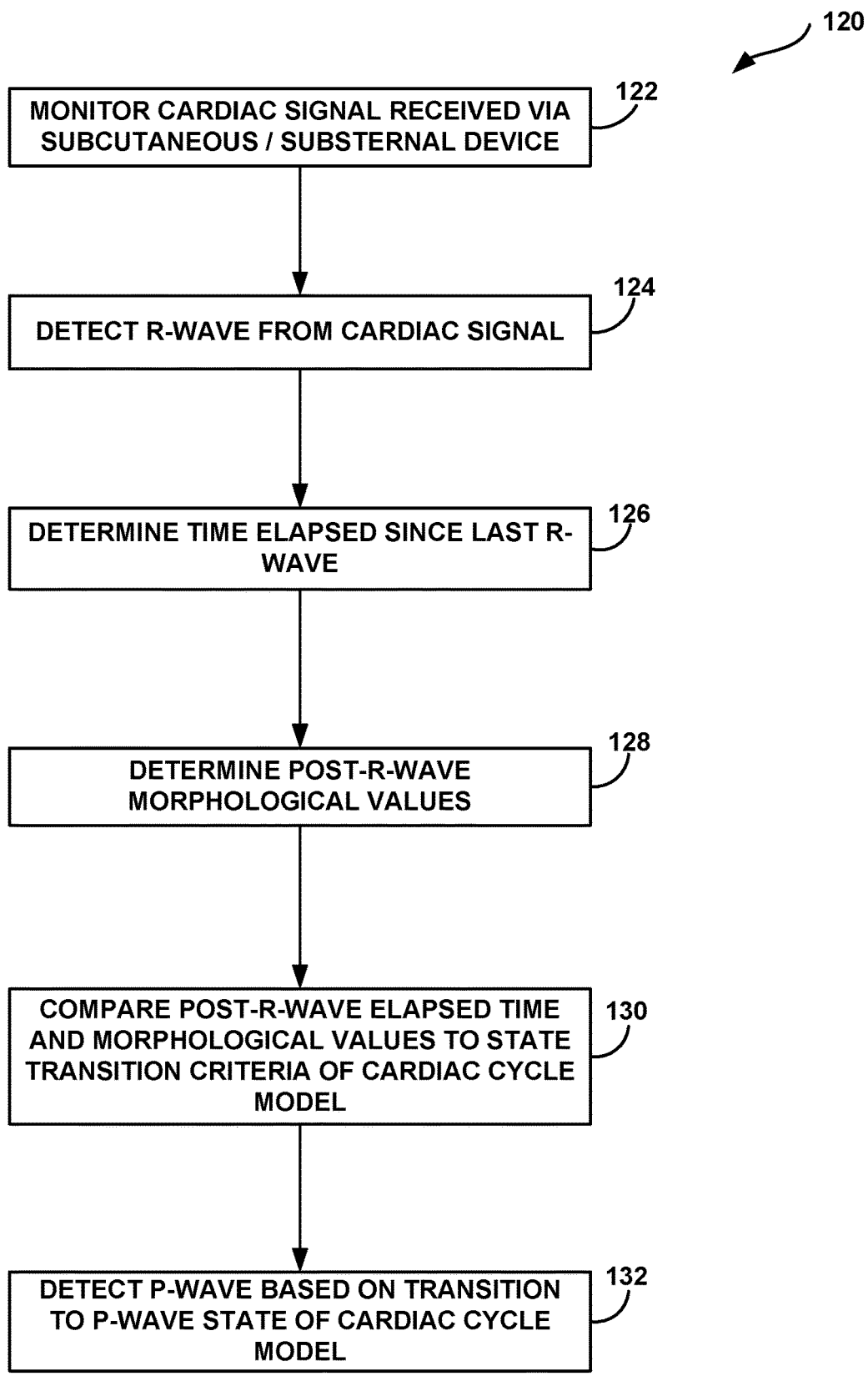
FIG. 8 is a flowchart illustrating an example process which an IMD system may perform to implement one or more P-wave detection techniques of this disclosure.

FIG. 8 is a flowchart illustrating an example process 120 by which IMD 10 and/or various components thereof may perform to implement one or more P-wave detection techniques of this disclosure. As part of process 120, sensing circuitry 66 may monitor or sense a cardiac signal of patient 14 via electrodes that are implanted, e.g., substernally or subcutaneously, within the body of the patient (122). Processing circuitry 60 may detect first R-wave state 82A from the cardiac signal (124). For instance, processing circuitry 60 may receive an indication from sensing circuitry 66, or itself detect, that the amplitude of the signal has satisfied an R-wave detection threshold. In various examples, upon sensing R-wave state 82A, processing circuitry 60 may evaluate the sensed data with the timing and morphological parameters described above, to more completely characterize the sensed data as an R-wave (as opposed to a P-wave or T-wave). Processing circuitry 60 may, in some examples, also adjust the R-wave sensing parameters based on results of waveform classification, such as by making the parameters more sensitive or less sensitive. The post-sensing evaluation may be beneficial, because R-wave sensing may not represent a fully accurate process in all scenarios, and also because T-wave oversensing and/or P-wave oversensing can possibly occur.

Timing analyzer 76 of processing circuitry 60 may determine the time elapsed since the occurrence of first R-wave 82A (126). More specifically, timing analyzer 76 of processing circuitry 60 may continually monitor the length of time that has elapsed since the occurrence of first R-wave 82A. The various readings of the time elapsed since first R-wave 86A are represented in the state transition probability function of FIG. 7, for which the variable t_cycle is an input/parameter. Cardiac signal analyzer 74 of processing circuitry 60 may determine post-R-wave morphological values of the cardiac signal sensed by sensing circuitry 66 (128). For instance, cardiac signal analyzer 74 may determine various sets of Haar wavelet coefficients on a sample-by-sample basis using the sensed cardiac signal. State detector 78 of processing circuitry 60 may compare the elapsed time after first R-wave 82A and the morphological values to transition criteria of a cardiac cycle model (130).

For instance, memory 72 of IMD 10 may store the transition criteria for various post-R-wave states. The transition criteria may be expressed as a combination of temporal information and morphological information. One set of transition criteria may correspond to state transition probability $p_{45}$ which indicates a transition of the cardiac signal into P-wave state 92. If the combination of the elapsed time and the corresponding morphological values sufficiently match the transition criteria stored to memory 72 for state transition probability $p_{45}$, then state detector 78 of processing circuitry 60 may determine that the cardiac cycle of patient 14A has entered P-wave state 92 of the cardiac cycle model stored to memory 72 (132). That is, by using the techniques of this disclosure, state detector 78 of processing circuitry 60 may detect the occurrence of P-wave state 92 before the end of the atrial depolarization that manifests as the P-wave morphology detected by cardiac signal analyzer 74. By detecting P-wave state 92 before the end of the corresponding atrial depolarization of heart 16A, state detector 78 may enable IMD 10 (in cases where IMD 10 includes therapy generation circuitry 70) to deliver pacing therapy via defibrillation electrodes 20, in conjunction with or closer temporal proximity to the atrial depolarization of heart 16A that is associated with P-wave state 92.

In some examples, in addition to the time interval and morphology parameters discussed above, state detector 78 may also use a confidence parameter to detect state transitions. State detector 78 may modify the state transition probability function by narrowing or expanding the range of t_cycle values having non-zero transition probabilities, thereby narrowing or expanding the window size of where to expect/anticipate the next P-wave or the next T-wave. The confidence parameter would vary with how well the morphology parameters match the expected waveforms and/or the degree of noise in the signal, as examples.

The techniques described in this disclosure, including those attributed to the IMD, the programmer, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. A medical device comprising:
a memory configured to store criteria for transitioning between a plurality of states of a cardiac cycle model, the plurality of states including a second wave state;
sensing circuitry configured to sense a cardiac signal that varies as a function of a cardiac cycle of a patient; and
processing circuitry configured to:
detect a first wave in the sensed cardiac signal;
determine an elapsed time since the detection of the first wave;
determine one or more morphological values of a post-first wave segment of the cardiac signal occurring after the detection of the first wave;
compare the elapsed time and the one or more morphological values to the stored criteria for transitioning between the plurality of states of the cardiac cycle model;
determine whether a second wave is detected in the sensed cardiac signal based on whether a transition to the second wave state of the cardiac cycle model occurred; and
provide an indication based on whether the second wave is detected, wherein a therapy is delivered to the patient based on the indication.

2. The medical device of claim 1, wherein the first wave comprises an R-wave, the second wave comprises a P-wave, and the second wave state comprises a P-wave state.

3. The medical device of claim 2,
wherein the processing circuitry is configured to detect the P-wave based on occurrence of a transition to the P-wave state of the cardiac cycle model,
wherein the medical device further comprises communication circuitry configured to send a signal to another medical device configured to deliver a cardiac pacing pulse to the patient,
wherein the signal is configured to trigger the other medical device to deliver the cardiac pacing pulse at a predetermined time after the detection of the P-wave, and
wherein, to provide the indication based on whether the second wave is detected, the processing circuitry is configured to control the communication circuitry to send the signal to the other medical device in response to detecting the P-wave.

4. The medical device of claim 2,
wherein the processing circuitry is configured to detect the P-wave based on occurrence of a transition to the P-wave state of the cardiac cycle model,
wherein the medical device further comprises therapy generation circuitry configured to deliver a cardiac pacing pulse, and
wherein, to provide the indication based on whether the second wave is detected, the processing circuitry is configured to control the therapy generation circuitry to deliver the cardiac pacing pulse in response to detecting the P-wave.

5. The medical device of claim 1, wherein the criteria comprise probability functions, each of the probability functions determining a probability of a respective state transition as a function of the elapsed time and at least one of the one or more morphological values, and wherein the processing circuitry is configured to determine that the respective state transition has occurred in response to the probability meeting a threshold.

6. The medical device of claim 1, wherein the processing circuitry is configured to apply one or more time-frequency transformations to the post-first wave segment of the cardiac signal, and determine the one or more morphological values based on the application of the one or more time-frequency transformations to the post-first wave segment of the cardiac signal.

7. The medical device of claim 1, wherein the processing circuitry is configured to:
determine a plurality of morphological values of the post-first wave segment;
form multiple value profiles of the plurality of morphological values of the post-first wave segment, wherein each respective value profile corresponds to a respective state of the plurality of states of the cardiac cycle model; and
compare each value profile of the post-first wave segment to a respective corresponding value profile of the stored criteria.

8. The medical device of claim 1, wherein the processing circuitry is configured to determine one or more wavelet coefficients associated with the cardiac signal sensed by the sensing circuitry as the one or more morphological values.

9. The medical device of claim 1, wherein the sensing circuitry is further configured to sense a respiratory signal that varies as a function of a respiratory cycle of a patient, and wherein the processing circuitry is further configured to update the criteria stored in the memory based on one or more characteristics of the sensed respiratory signal.

10. The medical device of claim 9, wherein the processing circuitry is configured to modulate a temporal component of the criteria based on one or more characteristics of the sensed respiratory signal.

11. The medical device of claim 1, further comprising a housing configured for implantation within patient, wherein the memory and the processing circuitry are located within the housing.

12. A method comprising:
storing criteria for transitioning between a plurality of states of a cardiac cycle model, the plurality of states including a second wave state;
sensing a cardiac signal that varies as a function of a cardiac cycle of a patient;
detecting a first wave in the sensed cardiac signal;
determining an elapsed time since the detection of the first wave;
determining one or more morphological values of a post-first wave segment of the cardiac signal occurring after the detection of the first wave;
comparing the elapsed time and the one or more morphological values to the stored criteria for transitioning between the plurality of states of the cardiac cycle model;
determining whether a second wave is detected in the sensed cardiac signal based on whether a transition to the second wave state of the cardiac cycle model occurred; and
providing an indication based on whether the second wave is detected, wherein a therapy is delivered to the patient based on the indication.

13. The method of claim 12, wherein the first wave comprises an R-wave, the second wave comprises a P-wave, and the second wave state comprises a P-wave state.

14. The method of claim 13, further comprising detecting the P-wave based on occurrence of a transition to the P-wave state of the cardiac cycle model,
wherein providing the indication comprises, in response to detecting the P-wave, sending a signal to another medical device configured to deliver a cardiac pacing pulse to the patient, wherein the signal is configured to trigger the other medical device to deliver the cardiac pacing pulse at a predetermined time after the detection of the P-wave.

15. The method of claim 13, further comprising detecting the P-wave based on occurrence of a transition to the P-wave state of the cardiac cycle model,
wherein providing the indication comprises, controlling delivery of a cardiac pacing pulse in response to detecting the P-wave.

16. The method of claim 12, wherein the criteria comprise probability functions, each of the probability functions determining a probability of a respective state transition as a function of the elapsed time and at least one of the one or more morphological values, the method further comprising determining that the respective state transition has occurred in response to the probability meeting a threshold.

17. The method of claim 12, further comprising:
applying one or more time-frequency transformations to the post-first wave segment of the cardiac signal; and
determining the one or more morphological values based on the application of the one or more time-frequency transformations to the post-first wave segment of the cardiac signal.

18. The method of claim 12, further comprising:
determining a plurality of morphological values of the post-first wave segment;
forming multiple value profiles of the plurality of morphological values of the post-first wave segment, wherein each respective value profile corresponds to a respective state of the plurality of states of the cardiac cycle model; and
comparing each value profile of the post-first wave segment to a respective corresponding value profile of the stored criteria.

19. The method of claim 12, further comprising determining one or more wavelet coefficients associated with the cardiac signal sensed by the sensing circuitry as the one or more morphological values.

20. The method of claim 12, further comprising:
sensing a respiratory signal that varies as a function of a respiratory cycle of a patient; and
updating the stored criteria based on one or more characteristics of the sensed respiratory signal.

21. The method of claim 20, wherein updating the stored criteria comprises modulating a temporal component of the criteria based on one or more characteristics of the sensed respiratory signal.

22. A medical device comprising:
a memory configured to store criteria for transitioning between a plurality of states of a cardiac cycle model, the plurality of states including a second wave state;
sensing circuitry configured to sense a cardiac signal that varies as a function of a cardiac cycle of a patient; and
processing circuitry configured to:
detect a first wave in the sensed cardiac signal;
determine an elapsed time since the detection of the first wave;
determine one or more morphological values of a post-first wave segment of the cardiac signal occurring after the detection of the first wave;
compare the elapsed time and the one or more morphological values to the stored criteria for transitioning between the plurality of states of the cardiac cycle model; and
determine whether a second wave is detected in the sensed cardiac signal based on whether a transition to the second wave state of the cardiac cycle model occurred.

23. The medical device of claim 22, wherein the processing circuitry is configured to control operation of at least one of the medical device or another medical device based on the determination of whether the second wave is detected.

* * * * *